United States Patent
Bartolucci et al.

(10) Patent No.: US 12,280,573 B2
(45) Date of Patent: *Apr. 22, 2025

(54) BIODEGRADABLE AND/OR HOME COMPOSTABLE SACHET CONTAINING A SOLID ARTICLE

(71) Applicant: The Procter & Gamble Company, Cincinnati, OH (US)

(72) Inventors: Stefano Bartolucci, Singapore (SG); Emily Charlotte Boswell, Cincinnati, OH (US); Su Anne Lee, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 186 days.

This patent is subject to a terminal disclaimer.

(21) Appl. No.: 18/106,099

(22) Filed: Feb. 6, 2023

(65) Prior Publication Data

US 2023/0173799 A1 Jun. 8, 2023

Related U.S. Application Data

(63) Continuation of application No. 17/070,205, filed on Oct. 14, 2020, now Pat. No. 11,597,191.

(Continued)

(51) Int. Cl.
*B32B 27/10* (2006.01)
*B32B 7/05* (2019.01)
(Continued)

(52) U.S. Cl.
CPC ............... *B32B 27/10* (2013.01); *B32B 7/05* (2019.01); *B32B 7/12* (2013.01); *B32B 23/08* (2013.01);
(Continued)

(58) Field of Classification Search
None
See application file for complete search history.

(56) References Cited

U.S. PATENT DOCUMENTS

| 1,421,350 A | 6/1922 | Powell |
| 2,356,168 A | 8/1944 | Mabley |

(Continued)

FOREIGN PATENT DOCUMENTS

| CA | 169627 S | 5/2018 |
| CN | 1138091 A | 12/1996 |

(Continued)

OTHER PUBLICATIONS

"Green Chemistry", Huazhong University of Science and Technology Press, published on Jun. 30, 2008, pp. 6.

(Continued)

*Primary Examiner* — James C Yager
(74) *Attorney, Agent, or Firm* — Alexandra S. Anoff

(57) ABSTRACT

A sachet product that includes a biodegradable and/or home compostable sachet comprising a front film and a back film. In some examples, the front film and back film can include a middle layer that can contain paper with greater than 85% cellulose and an inner layer that can include different material, including but not limited to polyvinyl alcohol or polyhydroxylalkonate. The sachet can include a compartment adapted for storing a solid article where the solid article is an open cell foam. The open cell foam can include a water-soluble polymer and a surfactant.

20 Claims, 7 Drawing Sheets

Related U.S. Application Data

(60) Provisional application No. 62/914,972, filed on Oct. 14, 2019.

(51) Int. Cl.
  *B32B 7/12* (2006.01)
  *B32B 23/08* (2006.01)
  *B32B 27/18* (2006.01)
  *B32B 27/30* (2006.01)
  *B32B 27/36* (2006.01)

(52) U.S. Cl.
  CPC ............ *B32B 27/18* (2013.01); *B32B 27/306* (2013.01); *B32B 27/36* (2013.01); *B32B 2250/24* (2013.01); *B32B 2305/30* (2013.01); *B32B 2307/31* (2013.01); *B32B 2307/5825* (2013.01); *B32B 2307/7163* (2013.01); *B32B 2329/04* (2013.01); *B32B 2367/00* (2013.01); *B32B 2391/00* (2013.01); *B32B 2439/06* (2013.01)

(56) References Cited

U.S. PATENT DOCUMENTS

| | | |
|---|---|---|
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,236,733 A | 2/1966 | Karsten et al. |
| 3,321,425 A | 5/1967 | Karl-Ludwig et al. |
| 3,332,880 A | 7/1967 | Adriaan et al. |
| 3,426,440 A | 2/1969 | Shen et al. |
| 3,428,478 A | 2/1969 | Donaldson et al. |
| 3,463,308 A | 8/1969 | Deneke |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin |
| 3,967,921 A | 7/1976 | Haberli et al. |
| 4,020,156 A | 4/1977 | Murray et al. |
| 4,024,078 A | 5/1977 | Gilbert et al. |
| 4,051,081 A | 9/1977 | Jabs et al. |
| 4,089,945 A | 5/1978 | Brinkman et al. |
| 4,149,551 A | 4/1979 | Benjamin et al. |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De Marco et al. |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |
| 4,663,158 A | 5/1987 | Wolfram et al. |
| 4,710,374 A | 12/1987 | Grollier et al. |
| 4,723,362 A | 2/1988 | Boerger |
| 4,727,410 A | 2/1988 | Higgins |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| D351,345 S | 10/1994 | Geho |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,458,433 A | 10/1995 | Stastny |
| 5,476,597 A | 12/1995 | Sakata et al. |
| 5,501,238 A | 3/1996 | Borstel et al. |
| 5,533,636 A | 7/1996 | Reiker |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| D399,260 S | 10/1998 | Thimote |
| 5,849,378 A | 12/1998 | Gask |
| D407,640 S | 4/1999 | Crapser et al. |
| D408,223 S | 4/1999 | Henry |
| 5,911,224 A | 6/1999 | Berger |
| 5,925,603 A | 7/1999 | D Angelo |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D479,561 S | 9/2003 | Meyer |

(56) References Cited

U.S. PATENT DOCUMENTS

| | | |
|---|---|---|
| D484,749 S | 1/2004 | Garraway |
| D489,162 S | 5/2004 | Dings-plooij |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| D509,935 S | 9/2005 | Burt |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D576,753 S | 9/2008 | Mukai |
| D577,332 S | 9/2008 | Moore |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| 7,985,266 B2 | 7/2011 | Zhang et al. |
| D644,541 S | 9/2011 | Schrader et al. |
| D651,096 S | 12/2011 | Nakagiri |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| D712,159 S | 9/2014 | Clerici et al. |
| D712,822 S | 9/2014 | Brusaw et al. |
| 9,062,186 B2 | 6/2015 | Longdon et al. |
| D739,227 S | 9/2015 | Mitchell et al. |
| D740,928 S | 10/2015 | Bruining et al. |
| 9,198,838 B2 | 12/2015 | Glenn, Jr. |
| D748,240 S | 1/2016 | Goode |
| D769,522 S | 10/2016 | Venet |
| D771,788 S | 11/2016 | Duckwitz |
| D774,086 S | 12/2016 | Montes et al. |
| D775,198 S | 12/2016 | Montes et al. |
| 9,539,444 B2 | 1/2017 | Kinoshita et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noël |
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,694,917 B2 | 6/2020 | Dreher et al. |
| D901,115 S | 11/2020 | Carlson et al. |
| D903,152 S | 11/2020 | Chao |
| D906,802 S | 1/2021 | Chi |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 11,597,121 B2 | 3/2023 | Wilson et al. |
| 11,597,191 B2 | 3/2023 | Bartolucci et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan |
| 2003/0099691 A1 | 5/2003 | Lydzinski et al. |
| 2003/0099692 A1 | 5/2003 | Lydzinski et al. |
| 2003/0141662 A1 | 7/2003 | Kost et al. |
| 2003/0166489 A1 | 9/2003 | Van Asten et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0118852 A1 | 6/2004 | Barmore et al. |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0118237 A1 | 6/2005 | Krzysik et al. |
| 2005/0136780 A1 | 6/2005 | Clark et al. |
| 2005/0137272 A1 | 6/2005 | Gaserod |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |

(56) References Cited

U.S. PATENT DOCUMENTS

| | | |
|---|---|---|
| 2006/0013869 A1 | 1/2006 | Ignatious |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0276178 A1 | 11/2008 | Fadell et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0143678 A1 | 6/2010 | Reilly et al. |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0279905 A1 | 11/2010 | Glenn, Jr. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0105946 A1 | 4/2014 | Glenn, Jr. et al. |
| 2014/0271744 A1 | 9/2014 | Glenn, Jr. et al. |
| 2014/0329428 A1 | 11/2014 | Glenn, Jr. |
| 2015/0102307 A1 | 4/2015 | Tajima et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0101026 A1 | 4/2016 | Pratt |
| 2016/0101204 A1 | 4/2016 | Lynch |
| 2016/0143827 A1 | 5/2016 | Castan Barberan et al. |
| 2016/0250109 A1 | 9/2016 | Dreher et al. |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0110710 A1 | 4/2018 | Zhao et al. |
| 2018/0140469 A1 | 5/2018 | Kane et al. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2019/0015875 A1 | 1/2019 | Gardner, Jr. et al. |
| 2019/0193905 A1 | 6/2019 | Reynoso |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0214946 A1 | 7/2020 | Chan et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0147763 A1 | 5/2021 | Tan et al. |
| 2021/0401677 A1 | 12/2021 | Song |

FOREIGN PATENT DOCUMENTS

| | | |
|---|---|---|
| CN | 1219388 A | 6/1999 |
| CN | 1268558 A | 10/2000 |
| CN | 1357613 A | 7/2002 |
| CN | 1454231 A | 11/2003 |
| CN | 1468284 A | 1/2004 |
| CN | 1473194 A | 2/2004 |
| CN | 1476467 A | 2/2004 |
| CN | 1530431 A | 9/2004 |
| CN | 1583991 A | 2/2005 |
| CN | 1726074 A | 1/2006 |
| CN | 3648760 A | 5/2007 |
| CN | 102006852 A | 4/2011 |
| CN | 301666535 A | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 A | 4/2017 |
| CN | 106726634 A | 5/2017 |
| CN | 106728634 A | 5/2017 |
| CN | 304537587 A | 3/2018 |
| CN | 109072143 A | 12/2018 |
| CN | 109589279 B | 3/2020 |
| DE | 19607851 A1 | 9/1997 |
| DE | 10331767 A1 | 2/2005 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1214879 A2 | 6/2002 |
| EP | 1217987 B1 | 12/2004 |
| EP | 1574561 A1 | 9/2005 |
| EP | 1160311 B1 | 3/2006 |
| EP | 1958532 A2 | 8/2008 |
| EP | 2085434 A1 | 8/2009 |
| EP | 1317916 B1 | 10/2010 |
| FR | 2871685 A1 | 12/2005 |
| FR | 2886845 A1 | 12/2006 |
| GB | 2235204 A | 2/1991 |
| GB | 2355008 A | 4/2001 |
| GB | 2378407 A | 2/2003 |
| JP | 58021608 A | 2/1983 |
| JP | S58216109 A | 12/1983 |
| JP | S6272609 A | 4/1987 |
| JP | S6272610 A | 4/1987 |
| JP | S6281432 A | 4/1987 |
| JP | H01172319 A | 7/1989 |
| JP | H01313418 A | 12/1989 |
| JP | H0275650 A | 3/1990 |
| JP | H05344873 A | 12/1993 |

(56) References Cited

FOREIGN PATENT DOCUMENTS

| | | | |
|---|---|---|---|
| JP | H0617083 A | 1/1994 |
| JP | 0753349 A | 2/1995 |
| JP | H0789852 A | 4/1995 |
| JP | H08325133 A | 12/1996 |
| JP | H09216909 A | 8/1997 |
| JP | H10251371 A | 9/1998 |
| JP | H11513053 A | 11/1999 |
| JP | 2000053998 A | 2/2000 |
| JP | 2000229841 A | 8/2000 |
| JP | 2001519376 A | 10/2001 |
| JP | 2001520983 A | 11/2001 |
| JP | 2002226895 A | 8/2002 |
| JP | 2003073700 A | 3/2003 |
| JP | 2003082397 A | 3/2003 |
| JP | 2004509198 A | 3/2004 |
| JP | 2004256799 A | 9/2004 |
| JP | 2004345983 A | 12/2004 |
| JP | 2005171063 A | 6/2005 |
| JP | 2005538202 A | 12/2005 |
| JP | 2006056835 A | 3/2006 |
| JP | 2007001889 A | 1/2007 |
| JP | 2007091954 A | 4/2007 |
| JP | 2007197365 A | 8/2007 |
| JP | 2007197540 A | 8/2007 |
| JP | 2012515835 A | 7/2012 |
| JP | 2014504236 A | 2/2014 |
| KR | 20020003442 A | 1/2002 |
| RU | 2424121 C2 | 7/2011 |
| WO | 8301943 A1 | 6/1983 |
| WO | 9514495 A1 | 6/1995 |
| WO | 9951715 A1 | 10/1999 |
| WO | 0042992 A2 | 7/2000 |
| WO | 0107194 A1 | 2/2001 |
| WO | 0119948 A1 | 3/2001 |
| WO | 0125393 A1 | 4/2001 |
| WO | 200125382 A1 | 4/2001 |
| WO | 2001024770 A1 | 4/2001 |
| WO | 2001054667 A1 | 8/2001 |
| WO | 0238722 A2 | 5/2002 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2005075547 A1 | 8/2005 |
| WO | 2007033598 A1 | 3/2007 |
| WO | 2007093558 A1 | 8/2007 |
| WO | 2007102119 A1 | 9/2007 |
| WO | 2008104954 A2 | 9/2008 |
| WO | 2009019571 A2 | 2/2009 |
| WO | 2009095891 A1 | 8/2009 |
| WO | 2010077627 A2 | 7/2010 |
| WO | 2010085569 A1 | 7/2010 |
| WO | 2012120199 A1 | 9/2012 |
| WO | DM100932 | 4/2018 |
| WO | DM100938 | 4/2018 |
| WO | DM101063 | 5/2018 |
| WO | DM101100 | 5/2018 |
| WO | DM101101 | 5/2018 |
| WO | 2019001940 A1 | 1/2019 |

OTHER PUBLICATIONS

"Product Review: Gemz Solid Shampoo", Travel as Much.Com, published on Mar. 19, 2019, retrieved on Apr. 27, 2021, retrieved from the Internet URL: https://travelasmuch.com/gemz-solid-shampoo-review/, 14 pages.
Adhesives Research (Pennsylvania, http://12.4.33.51/news/apresmed.htm) (No Known Date).
All Office Actions; U.S. Appl. No. 17/070,205, filed Oct. 14, 2020.
Amerilab Technologies, Inc. (Minnesota, http://www.amerilabtech.com/) (No Known Date).
Anonymous "P8136 Poly(vinyl alcohol)" Internet article, [Online] XP002538935, Retrieved from the Internet: URL:hllp/20 NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009, year 2009, 1 pg.
Briscoe et al. "The effects of hydrogen bonding upon the viscosity of aqueous poly( vinyl alcohol) solutions," Polymer, vol. 41, No. 2000, accepted on Jul. 30, 1999, pp. 3851-3860.
Cardinal Health (Dublin, Ohio, http://spd.cardinal.com/) (No Known Date).
Cima Labs, Inc. (Minnesota, http://www.cimalabs.com/) (No Known Date).
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDa1Nuo9_cQSOpPwCmsmmdGA1Y0USekQEaAh0iEALw_wcB (Year: 2021).
Design of "Detergent tablets" (Design Registration No. 000634142-0003), (No. of Publicly known information: HH18274488), Registered Community Designs Bulletin, published by EUIPO on Jan. 9, 2007, 4 pgs.
Design of "Detergent tablets" (Design Registration No. 000634142-0004), (No. of Publicly known information: HH18274489), Registered Community Designs Bulletin, published by EUIPO on Jan. 9, 2007, 4 pgs.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612), 3 pgs.
Dissolving Soap Strips (Ranir LLC, Michigan, www.ranir.com) ( Copy not provided)(No Known Date).
Dow, UCAR Polymer LR-400, Technical Data Sheet, Downloaded in Mar. 2022, 4 pages.
Encyclopedia of Polymer Science and Engineering, vol. 15, 2nd ed., pp. 204 308 Silicones, year 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, New Silicon mold, Published on Sep. 29, 2016, Retrieved from Internet : http://candle-box.com/product/%EC%9C%A1%EA%B0%81-4%EA%B5%AC-%EB%B9%84%EB%88%84%EB%AA%B0%EB%93%9C/2206/?page_4=3#none, dated Sep. 10, 2019, 16 pages.
Hexagon Craft Shape, Craftcuts, Retrieve from: https ://www.craftcuts.com/hexagon-craft-shape.html, Hexagon wood cutouts, www.craftcuts.com, reviewed as early as May 2018 (Year: 2018), 1 page.
Hildebrand, T., et al. "Quantification of bone microarchitecture with the structure mode index", Computer Methods in Biomechanics and Biomedical Engineering, vol. 1, Jan. 14, 1997, pp. 15-23.
Hiroshi Yagi & 4 Others, Research Study of a Friction Protector for Preventing a Tow Line From Breaking, Working Papers for Fiscal 2006 | Japan | Japan Coast Guard |Dec. 2007, pp. 1-8.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pages.
Search Report and Written Opinion for PCT/US2020/070665 dated Jan. 28, 2021; 10 pages.
Japanese Paper Soap (http://www.wishingfish.com/papersoap.html) (No Known Date).
Karen Duis et al., "Environmental fate and effects of water-soluble synthetic organic polymers used in cosmetic products", Environmental Sciences Europe, vol. 33, Article No. 21, Feb. 16, 2021, 78 pages.
Kuraray: "Mowiol-Technical data sheet", Jun. 1, 2010 (Jun. 1, 2010), Retrieved from the Internet: URL:http://www.kuraray.eu/fileadmin/Downloads/mowiol/TDS_Mowiol_en_20110624.pdf [retrieved on May 23 2014].
Latorre Carmen, Nanotribological Effects of Hair Careproducts and Environment on Human Hair Using Atomic Forcemicroscopy,Journal of Vacuum Science and Technology: Part A, U.S.A, AVS/AIP , Jun. 28, 2005 , V2 3 N 4, p. 1034-1045.
Le Laboratoire du Bain (France, http://www.laboudubain.com/) (No known date).

(56) References Cited

OTHER PUBLICATIONS

M.K. Industries (Gujarat India, http://www.soapstrips.com) (No known date).

Meguiars Car Wash Strips: Meguiars Inc. California, http://www.automotivedigest.com/view_art.asp?articlesID=12414 (No known date).

Merriam Webster, "Definition of Derivative", dated Aug. 11, 2021, https://www.merriam-webster.com/dictionary/derivative, 1 page.

Michelle Villett, Why You Need a Sulfate-Free Shampoo, The Skincare Edit, updated on Jan. 25, 2019, Original publication date: Feb. 22, 2016 (Year: 2016), 7 pages.

MOVA Pharmaceutical and Kosmos (USA, http://www.icon-pr.com/news/news/prinl.cfm?inv_id=256-1) (No known date).

Ni Genshan et al. "Drug Classification and Pharmacology Summary", PLA Press, published on Apr. 30, 1988, pp. 3.

Okasaka et al., "Evaluation of Anionic Surfactants Effects on The Skin Barrier Function Based on Skin Permeability", Pharmaceutical Development and Technology, vol. 24, No. 1, Jan. 23, 2018, pp. 99-104.

Paper Pieces Hexagons Pack 1in 1200pc, announced 2018 [online], site visited Oct. 18, 2021, Available from internet, URL:https://www.amazon.com/Paper-Pieces-HEX100B-Hexagons-1200pc/dp/B07DVYV2HN/(Year: 2018), 5 pages.

Pure Soap Leafz: (Soap UNLTD. Netherlands, http://www.upandunder.com.uk/eshop/catalogue/testbs.asp?Manufacturer_ID=252&Activity_ID=33&Description_ID=157) (No known date).

Raymond C Rowe et al., "Polyvinyl Alcohol", Handbook of Pharmaceutical Excipients Sixth Edition, published in 2009 Pharmaceutical Press, pp. 564-565.

Rounded hexagon shape, announced 2016 [online], [site visited Oct. 20, 2021], Available from internet, URL:https://www.vexels.com/png-svg/preview/139199/rounded-hexagon-shape (Year: 2016), 4 pages.

Sahin et al. "A Study on Physical and Chemical Properties of Cellulose Paper Immersed in Various Solvent Mixtures" International Journal of Molecular Sciences, accepted on Jan. 10, 2008 Jan.; vol. 9, No. 1, pp. 78-88.

Sanipro Sanitary Products (Italy, http://www.sanipro.iit) (No known date).

Solublon (Toyohashi Japan, http://www.solublon.com) (No known date).

SPI Pharma (Delaware, http://www.spipharma.com) (No known date).

Travelers Passport Paper Soap Sheets (http://www.weddingflavornow.com/index.asp?PageAction=VIEWPROD&ProdID=510) (No known date).

Vaughan, C.D. "Solubility, Effects in Product, Package, Penetration and Preservation", Cosmetics and Toiletries, vol. 103, Oct. 1988, 24 pages.

Vesterby, A.: "Star Volume in Bone Research: A Histomorphometric Analysis of Trabecular Bone Structure Using Vertical Sections", The Anatomical Record 235, Accepted on Jun. 23, 1992, pp. 325-334.

Wenda (China, http://www.wenda.com) (No known date).

Wermuth, Similarity in Drugs: Reflections on Analogue Design, Drug Discovery, "Drug Discovery Today, 2006", vol. 11, No. 7/8, Apr. 2006, pp. 348-354.

Zhang et al. "Study on Morphology of Electrospun Poly( vinyl alcohol) Mats," European Polymer Journal, vol. 41, accepted on Oct. 20, 2004, available online on Dec. 24, 2004, pp. 423-432.

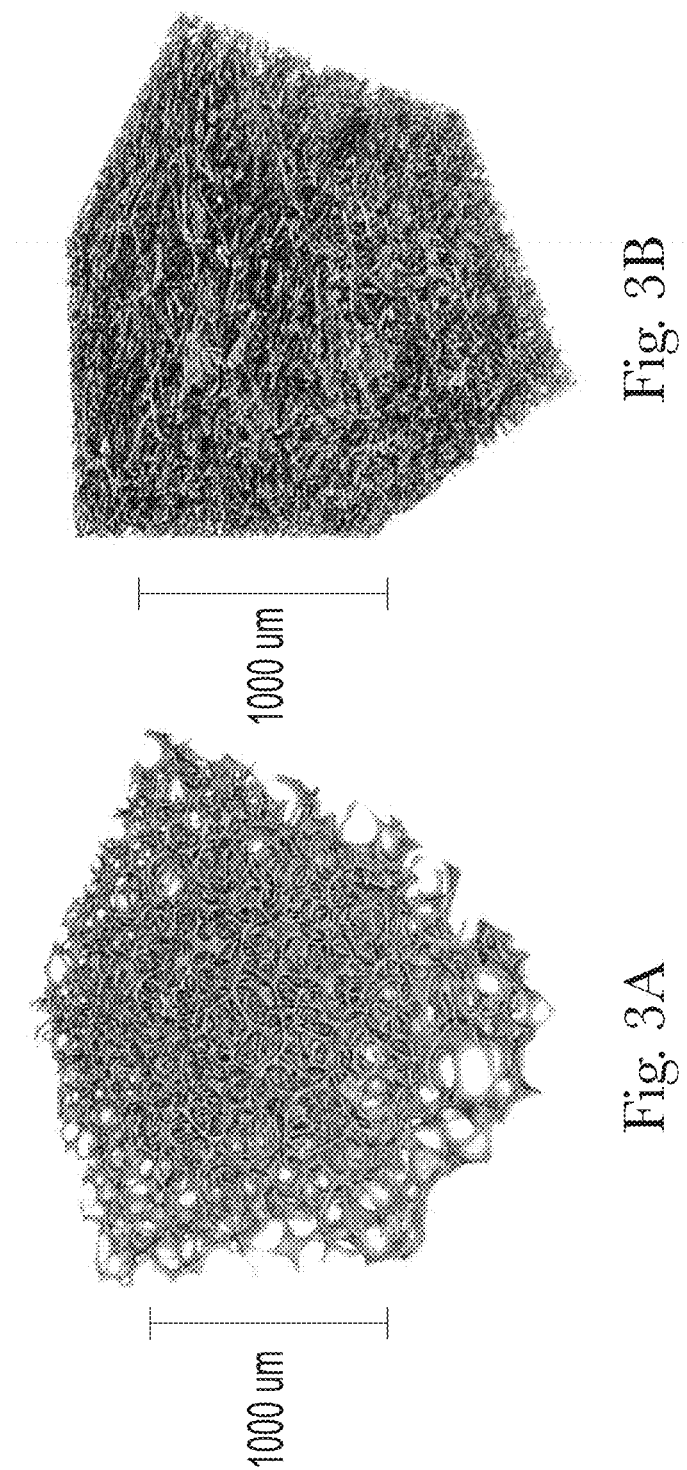

BIODEGRADABLE AND/OR HOME COMPOSTABLE SACHET CONTAINING A SOLID ARTICLE

FIELD OF THE INVENTION

The present invention is directed toward a sachet that contains a solid article, and more particularly, to a biodegradable and/or home compostable sachet containing an open cell foam article.

BACKGROUND OF THE INVENTION

Sachet packaging of small amounts of consumer products such as shampoo, conditioner, body wash, and other consumer products and laundry detergents can be desirable to consumers who want inexpensive, single use products. This includes people who cannot afford, cannot transport, and/or cannot store large containers that are typically found in developed countries.

Sachet packaging is generally made of a laminate film containing layers of plastic and aluminum. There is interest in using a biodegradable and/or home compostable sachet. However, there are many challenges with creating acceptable biodegradable and/or home compostable sachets, especially ones that store liquid products that can be sold and stored in non-climate controlled high frequency stores in humid climates. Many biodegradable and/or home compostable sachets have a high moisture vapor transmission rate (MVTR), which limits the practicality for consumer products due to high water loss (for liquid products) or water gain (for powders and other solid products).

It can be advantageous to sell solid articles in sachet packaging because (1) solid articles can be lightweight, as compared to a similar dose of a traditional liquid products; (2) solid articles can provide consistent dosing; and (3) there is considerably less product wasted, as compared to dispensing liquid product from a bottle or sachet.

Furthermore, the sachets can be subjected to relatively high compressive loads (up to about 20 psig/137.9 kPa) during shipping, storage, and at the point of sale. These compressive loads can damage the product and/or package.

Therefore, there is a need for a sachet for storing a solid single use consumer product where the sachet is biodegradable and/or home compostable, provides an acceptable moisture barrier, can withstand compressive loads of up to 20 psig (137.9 kPa), where the consumer product is shelf stable for at least 18 months, and that can be recycled in a paper repulping system or be organically recycled (e.g. via home composting or industrial composting where available).

SUMMARY OF THE INVENTION

A sachet product comprising a biodegradable and/or home compostable sachet comprising a front film and a back film comprising: (a) a front middle layer and a back middle layer comprising a paper having greater than 85% cellulose content; (b) a front inner layer joined to the front middle layer and a back inner layer joined to the back middle layer wherein the front inner layer and back inner layer comprises an inner layer material selected from the group consisting of polyvinyl alcohol, polybutylene succinate, polybutylene succinate adipate, polyhydroxylalkonate, polyvinylidene chloride, carnauba wax, biodegradable thermo-plastic starch, and combinations thereof; wherein front inner layer and back inner layer being permanently joined around a perimeter to form a seal, the seal forming a compartment adapted for storing a solid article comprising an open cell foam comprising: from about 10% to about 40%, by total weight of the article, of a water-soluble polymer; from about 5% to about 80%, by total weight of the article, surfactant selected from the group consisting of anionic surfactants, cationic surfactants, nonionic surfactants, amphoteric surfactants, zwitterionic surfactants, and combinations thereof; a Percent Open Cell Content of from about 80% to 100%; an Overall Average Pore Size of from about 100 μm to about 2000 μm.

A sachet product comprising a biodegradable and/or home compostable sachet comprising a front film and a back film comprising: (a) a front middle layer and a back middle layer comprise a material selected from the group consisting of cellulose, cellulose acetate, metalized cellulose, metalized cellulose acetate, and combinations thereof; (b) a front inner layer joined to the front outer layer and a back inner layer joined to the back outer layer wherein the front inner layer and the back inner layer comprise a material selected from the group consisting of polyvinyl alcohol, polybutylene succinate, polybutylene succinate adipate, polyhydroxylalkonate, carnauba wax, a biodegradable thermo-plastic starch, polyvinylidene chloride, and combinations thereof; wherein front inner layer and back inner layer being permanently joined around a perimeter to form a seal, the seal forming a compartment adapted for storing a solid article comprising an open cell foam comprising: from about 10% to about 40%, by total weight of the article, of a water-soluble polymer; from about 5% to about 80%, by total weight of the article, surfactant selected from the group consisting of anionic surfactants, cationic surfactants, nonionic surfactants, amphoteric surfactants, zwitterionic surfactants, and combinations thereof; a Percent Open Cell Content of from about 80% to 100%; an Overall Average Pore Size of from about 100 μm to about 2000 μm.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 3A shows a micro-CT scan of a portion of an open cell foam article;

FIG. 3B shows a micro-CT scan of a portion of a fibrous article;

DETAILED DESCRIPTION OF THE INVENTION

Figure 1A:
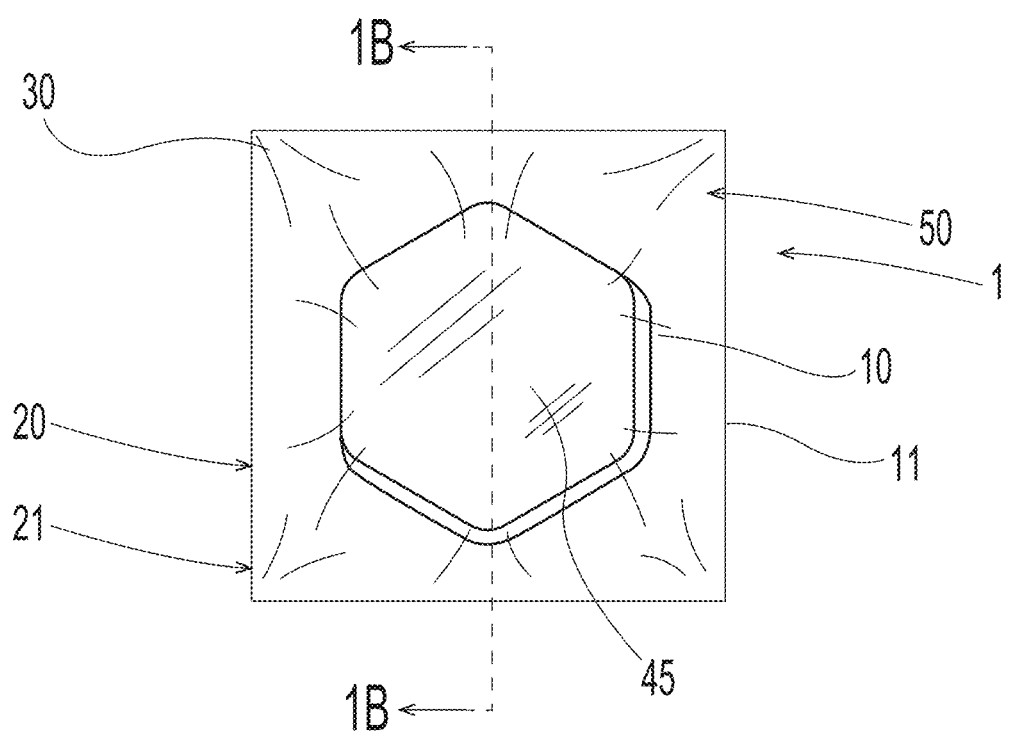
FIG. 1A is a perspective view of a sachet.

Some consumers may want solid articles containing personal care actives (e.g. shampoo, conditioner, body wash, etc.) and/or laundry actives (e.g. detergent, fabric softener, etc.). First, solid articles can be lightweight, as compared to a similar dose of a traditional liquid products that generally contain at least 80% water. Second, solid articles can provide consistent dosing since the consumer can have more precise control over the amount used. For example, she can easily use the entire article or a portion thereof, instead of haphazardly pouring liquid product from a sachet or bottle. Third, there is considerably less product wasted, as compared to dispensing liquid product from a bottle or sachet. Consumers in developing markets are particularly frustrated by wasted product because consumer products, like shampoo, conditioner and laundry products, are considered a luxury. Furthermore, consumer articles in solid form can provide performance benefits as compared to traditional articles.

Furthermore, solid articles can be stored in sachet packaging. Sachet packaging is commonly used to store small amounts of consumer products including shampoo, conditioner, and body wash and laundry products. Articles in sachets provide consumers with inexpensive, single use products. Many consumers who regularly use sachets are those who cannot afford, cannot transport, and/or cannot store large containers that are typically found in developed countries.

The sachets are typically sold in locally owned bodegas, stalls and kiosks, often referred to as "high-frequency stores," because of the multiple times shoppers visit them during a single day or week. Most of these stores are rudimentary, frequently operating out of the owner's home, small (e.g. the typical high-frequency store in Latin America is just 250 square feet) and not climate controlled. High-frequency stores are common in parts of Latin America, Asia including parts of China, India, and Indonesia, and Africa. The climate can be hot and humid and therefore the sachet needs to provide an effective moisture barrier to protect the article. This is important when the article is a solid article that becomes liquid upon hydration. If the sachet has an MVTR that is too high, then the humidity can seep into the article, resulting in a sticky article that can leave behind a residue upon removal from the sachet.

Furthermore, high-frequency store owners generally store the consumer product sachets in stacked boxes and hang just a few sachets from the ceiling. This means that the articles stored in the sachets are subject to a relatively high compressive load (up to about 20 psig/137.9 kPa) during shipping, handling, and at the store shelf. Furthermore, consumers often carry sachet products in their pockets or shopping bags or even squeeze the sachet at the store shelf, which can subject the article to further damage. Therefore, the sachet must protect the consumer article from this compressive load, especially when the article is a solid that has a porous structure, including fibrous structures and open cell foam structures. If the porous structure is subjected to too high of a compressive load, the compression pressure densifies the article irreversibly. This is particularly true when the article is stored in high relative humidity conditions. This densification makes it difficult to dissolve the article, making it inconvenient to use and/or less effective.

The sachet can store the solid article in an environment of up to 90% relative humidity and subjected to a compressive load of up to 20 psig (137.9 kPa). The sachet product can satisfy the Accelerated Stability Test and/or the Stability Test after a period of 2 weeks, 4 weeks, 8 weeks, 12 weeks, and/or 6 months. After storage of the sachet product under accelerated stability conditions for 2 weeks, 4 weeks, 8 weeks, 12 weeks, and/or 6 months the article can have a Hand Dissolution value of less than 15 strokes, alternatively less than 12 strokes, and alternatively less than 10 strokes.

The sachet can have an MVTR of from about 0.01 to about 50 g/sqm/day, alternatively of about 0.05 to about 40 g/sqm/day, alternatively about 0.1 to about 30 g/sqm/day, alternatively about 0.2 to about 15 g/sqm/day at 38° C./90% RH. Alternatively, the sachet can have an MVTR of from about 10 to about 1000 g/sqm/day, alternatively from about 12 to about 800 g/sqm/day at 38° C./90% RH. The sachet can have an MVTR of less than 500 g/sqm/day, alternatively less than 400 g/sqm/day, and alternatively less than 300 g/sqm/day. MVTR is measured according to the MVTR Test Method, described hereafter. If the KIT is greater than or equal to 6, according to the Grease Test, described hereafter, then the MVTR can be higher. If the KIT is less than or equal to 6, according to the Grease Test, described hereafter, then the MVTR can be lower.

The sachet can have a tear resistance less than 550 nM according to D1922-15, Elmendorf Method, MD tear direction.

The sachet can have a seal with a seal strength of from about 70 to about 700 N/m, from about 750 to about 650 N/m, alternatively from about 300 to about 600 N/m, alternatively from about 300 to about 500 N/m. The sachet can have a seal with a seal strength of greater than or equal to 75 N/m, alternatively greater than or equal to 100 N/m, and alternatively greater than or equal to 150 N/m. The sachet can have a seal strength less than 500 N/m, alternatively less than 400 N/m, and alternatively less than 250 N/m. Seal strength is measured according to the Average Seal Strength Test Method, described hereafter.

Definitions

As used herein, "aerate", "aerating" or "aeration" refers to a process of introducing a gas into a liquid or pasty composition by mechanical and/or chemical means.

As used herein, "controlled surface temperature" refers to a surface temperature that is relatively consistent, i.e., with less than +1-20% fluctuations, alternatively less than +1-10% fluctuations, alternatively less than +/−5% fluctuations.

As used herein, "dissolvable" refers to the ability of an article to completely or substantially dissolve in a sufficient amount of deionized water at 20° C. and under the atmospheric pressure within eight (8) hours without any stirring, leaving less than 5 wt % undissolved residues.

As used herein, "flexible" refers to the ability of an article to withstand stress without breakage or significant fracture when it is bent at 90° along a center line perpendicular to its longitudinal direction. Alternatively, such article can undergo significant elastic deformation and is characterized by a Young's Modulus of no more than 5 GPa, alternatively no more than 1 GPa, alternatively no more than 0.5 GPa, most alternatively no more than 0.2 GPa.

As used herein, "heating direction" refers to the direction along which a heat source applies thermal energy to an article, which results in a temperature gradient in such article that decreases from one side of such article to the other side. For example, if a heat source located at one side of the article applies thermal energy to said article to generate a temperature gradient that decreases from said one side to an opposing side, the heating direction is then deemed as extending from said one side to the opposing side. If both sides of such article, or different sections of such article, are heated simultaneously with no observable temperature gradient across such article, then the heating is carried out in a non-directional manner, and there is no heating direction As used herein, "home compostable" refers to materials that meet the pass levels for the OK compostable HOME OK-02e certification by TUV AUSTRIA (2012).

As used herein, "joined" refers to configurations in which a first element is directly secured to a second element. Joined also includes configurations in which the first element is indirectly secured to the second element.

As used herein, "include," "includes," and "including," are meant to be non-limiting and are understood to mean "comprise," "comprises," and "comprising," respectively.

As used herein, "molecular weight" or "Molecular weight" refers to the weight average molecular weight unless otherwise stated. Molecular weight is measured using industry standard method, gel permeation chromatography ("GPC").

As used herein, "open celled foam" or "open cell pore structure" refers to a solid, interconnected, polymer-containing matrix that defines a network of spaces or cells that contain a gas, typically a gas (such as air), without collapse of the foam structure during the drying process, thereby maintaining the physical strength and cohesiveness of the solid. The interconnectivity of the structure may be described by a Percent Open Cell Content, which is measured by Test 3 disclosed hereinafter.

As used herein, "permanently joined" refers to configurations in which a first element is secured to a second element such that the elements generally cannot be separated from one another without at least partially destroying one or both of the elements.

As used herein, "biodegradable" refers to materials that meet the pass levels for readily and ultimate biodegradability according to the OECD Guideline for Testing of Chemicals, Method 301 B: CO2 Evolution (Modified Sturm Test) (adopted Jul. 17, 1992).

As used herein, "recyclable" refers to used paper, including in-plant and post-consumer waste paper and paperboard, which is capable of being processed into new paper or paperboard using the process defined in the *Voluntary Standard for Repulping and Recycling Corrugated Fiberboard Treated to Improve its Performance in the Presence of Water and Water Vapor* (Aug. 16, 2013). In some examples, the sachet can be recyclable.

As used herein, "solid" refers to the ability of an article to substantially retain its shape (i.e., without any visible change in its shape) at 20° C. and under the atmospheric pressure, when it is not confined and when no external force is applied thereto.

As used herein, "sheet" refers to a non-fibrous structure having a three-dimensional shape, i.e., with a thickness, a length, and a width, while the length-to-thickness aspect ratio and the width-to-thickness aspect ratio are both at least about 5:1, and the length-to-width ratio is at least about 1:1. Alternatively, the length-to-thickness aspect ratio and the width-to-thickness aspect ratio are both at least about 10:1, alternatively at least about 15:1, most alternatively at least about 20:1; and the length-to-width aspect ratio is alternatively at least about 1.2:1, alternatively at least about 1.5:1, most alternatively at least about 1.618:1.

As used herein, "visual detection" means that a human viewer can visually discern the quality of the example with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of ⅓ meter.

As used herein, "water-soluble" refers to the ability of a sample material to completely dissolve in or disperse into water leaving no visible solids or forming no visibly separate phase, when at least about 25 grams, alternatively at least about 50 grams, alternatively at least about 100 grams, most alternatively at least about 200 grams, of such material is placed in one liter (1L) of deionized water at 20° C. and under the atmospheric pressure with sufficient stirring.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the personal care composition.

Biodegradable and/or Home Compostable Sachet

The sachet can be any sachet suitable for storing solid articles that can provide an effective moisture barrier, compression resilience, and be biodegradable and/or home compostable. The sachet can be a block bottom bag, a flat bag, a flowpack, a cross-bottom bag, a side gusset bags, a three-sided side sealed bag, a four-sided side sealed bag, a stand-up pouch, a stick pack, or a fully contoured pouch. The sachets can be connected and can be sold to stores, including high frequency stores, as a roll with a plurality of sachets that are connected end to end with perforations in between each sachet so the consumer can choose how many sachets she wants to purchase and tear them off the roll. In some examples, the perforations can be a zig-zag where the zig-zag makes it easier for the user to open the sachet. A roll of sachets can also have multiple sachets across that are separated by perforations (i.e. a multi-lane sachet with two, three, four, or more lanes). The sachet can have a pictorial usage instruction printed on at least one surface.

FIG. 1A is a perspective view of sachet 1 and in this example sachet 1 is a four-seal sachet. The sachet can be made from front film 10 with front perimeter 11 and back film 20 with back perimeter 21. Front perimeter 11 and back perimeter 21 are joined to one another at seal 30. The seal can be either irreversible (i.e. permanently joined) or reversible. In the examples presented, the seal is irreversible and obtained via a thermal contact bonding using an industrial impulse sealer. The seal strength can be optimized for a selected sealing material based on the sealing temperature, time, and pressure. While thermal sealing can be preferable, for cost, other seal welding methods are also possible such as ultrasonic welding, high-frequency welding, infrared welding, etc. or adhesive bonding as known by experts in the art. Front film 10 and back film 20 can be made from any biodegradable and/or home compostable material that provides an effective moisture barrier and compression resilience for the solid article. In some examples, front film 10 and back film 20 can be recyclable.

Sachet 1 can also comprise one or more tear notches 50. In order to open the sachet, a user tears the sachet open at the tear notch. The user can tear open a corner of the sachet or across the entire sachet. Tear notch 50 can be any size or shape that allows sachet 1 to be opened without the use of scissors or teeth. In one example, tear notch 50 can extend to the perimeter of the sachet. In another example, tear notch 50 can extend through front film 10 and back film 20. In one example, the sachet can include tear indicia, such as arrows or triangular arrowheads, that direct the user where to tear. The tear notch can extend from about 15% to about 75% across the heat seal, alternatively from about 25% to about 65%, alternatively from about 40% to about 60%, and alternatively from about 45% to about 55%.

The sachet 1 can comprise a printed area that is on or visible through the outer surface. Printing can be achieved using standard printing techniques, such as flexographic, gravure, or inkjet printing. In some examples, the outer surface can include a surface coating for artwork protection purposes against incidental moisture and/or for matt/gloss effects.

Figure 1B:
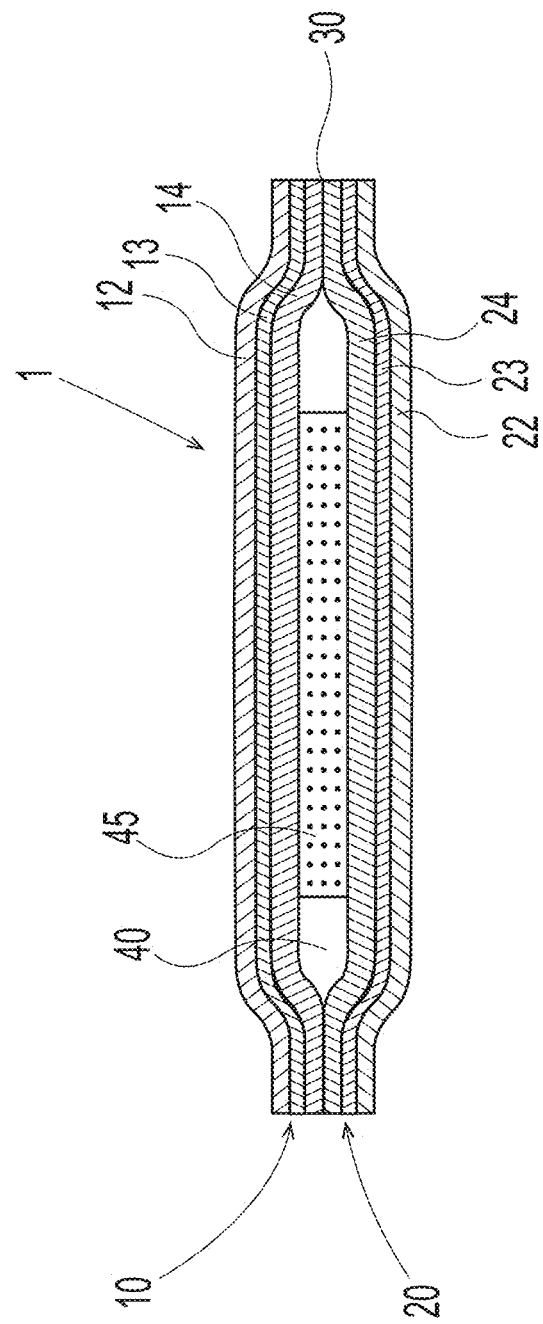
FIG. 1B is a cross-sectional view of a sachet taken along section line 1B-1B in FIG. 1A.

FIG. 1B is a cross-sectional view of sachet 1 along section line 1B-1B. In one example, front film 10 and back film 20 are made from a multi-layer structure. Front film 10 and back film 20 can be made from the same multi-layer structure or a different multi-layer structure.

As shown in FIG. 1B, front film 10 can comprise front outer layer 12, front middle layer 13, and front inner layer 14. Front outer layer 12 is joined to a first side of front middle layer 13 and front inner layer 14 is joined to a second, opposing side of front middle layer 13. Back film 20 can comprise back outer layer 22, back middle layer 23, and back inner layer 24. Front outer layer 22 is joined to a first side of front middle layer 23 and front inner layer 24 is joined to a second, opposing side of front middle layer 23. The layers of the film can be permanently joined. The layers of the film can be joined with or without adhesive. Front film 10 and back film 20, and more specifically front inner layer 14 and back inner layer 24, can be permanently joined in the heat seal 30 to form compartment 40, which is adapted for holding solid article 45. The width of the heat seal can be from about 1 mm to about 10 mm, alternatively from about 2 mm to about 7 mm, and alternatively from about 3 mm to about 5 mm.

The sachet can include front outer layer 12 and back outer layer 22 can be a surface coating. The coating can improve the moisture barrier properties of sachet, increase the durability of the underlaying film layer(s) including protecting the printed area, and/or provide an aesthetic finish (e.g. matte, glossy). In one example, front outer layer 12 and back outer layer 22 can comprise a readily biodegradable wax (e.g. beeswax, jojoba wax, carnauba wax). The front and back outer layers can be a lacquer, a varnish, or a splash-resistant layer. In some examples, the surface coating is made from a nitrocellulose lacquer, an acrylic lacquer, a water-based lacquer, a reactive two-components polyurethane lacquer. Biodegradable options can be preferred. In some examples, the surface coating is made from natural waxes passing the OECD301B biodegradation screening test, such as bees wax, rapeseed wax, castor wax, candelilla wax, soy wax, palm oil wax or another natural wax, provided that the temperature of exposure is not exceeding the wax melting point. In some cases, some paraffin oil-based waxes may also pass OECD301B. The thickness of the outer layer can affect the recyclability and/or the biodegradation of the sachet, thinner surface coatings may be more easily biodegraded. In some examples, each outer layer is a surface coating and can have a thickness between 0.1 μm to 25 μm, alternatively below 10 μm, and alternatively below 5 μm.

Front middle layer 13 and back middle layer 23 can comprise paper. Front and back middle layers can also be referred to as paper layers or biodegradable polymeric layers and can form the inner surface and/or outer surface of the sachet. The paper can comprise greater than 85% cellulose, alternatively greater than 90% cellulose, and alternatively greater than 95% cellulose. Alternatively, front middle layer 13 and back middle layer 23 can comprise a biodegradable paper which can also be recyclable in current paper recycling streams, where the paper contains cellulose in addition to additives including polymeric binders, mineral sizing agents, whitening agents, surfactants, etc. The additives can be selected to ensure that (a) the paper can biodegrade if improperly disposed in the environment and not cause any ecotoxicity issues, and/or (b) the paper can disintegrate in the repulping unit at a paper recycler and release the maximum cellulose fibers for making recycled paper.

The front middle layer and/or back middle layer can comprise from about 50% and about 100%, cellulose fibers, alternatively from about 65% to about 98%, cellulose fibers, alternatively from about 75% to about 95 cellulose fibers. The front and back middle layers can be the thickest layer in the front and/or back film and therefore a sachet package made thereof these middle layers can have a high biobased cellulose content by weight.

In some examples, the front and back middle layers can comprise recycled material, virgin material, or a mixture thereof. In some examples the front and/or back middle layer can contain greater than 80%, by weight of the layer, recycled material, alternatively greater than 85%, by weight of the layer, recycled material, alternatively greater than 90%, by weight of the layer, of recycled material, and alternatively greater than 95%, by weight, of recycled material. In some examples, the sachet can contain more than 10%, by weight, recycled material, alternatively more than 20%, by weight, alternatively more than 30%, by weight, alternatively more than 40%, by weight, recycled material, alternatively more than 50%, by weight, alternatively greater than 60%, by weight, alternatively greater than 70%, by weight, alternatively greater than 80%, by weight, recycled material.

The presence of recycled material can be made from a visual inspection of the package. For example, manufacturers typically advertise the use of recycled materials in an effort to demonstrate their eco-friendly product approach. To further expand on this example, some manufacturers may utilize a logo, e.g. a leaf, along with wording to indicate the use of recycled material in the package material. Often times, manufacturers may specify the percentage of recycled material utilized as well, e.g. over 50 percent, over 70 percent, etc. Visual inspection can be as simple as utilizing the human eye to inspect packages for logos of the use of recycled material. Additionally, or alternatively, visual inspection may include microscopy methods such as optical microscopy, scanning electron microscopy or other suitable methods known in the art. For example, package material comprising recycled paper fibers could look different under a microscope due to the presence of a much wider range of natural fiber types than if the package material comprised 100% non-recycled paper. As another example, under a microscope, potentially scanning electron microscope, recycled fibers, due to their processing may appear more fibrillated than their virgin fiber counterparts.

In some examples, to make the paper layers (e.g. front and back middle layers) flat as possible on at least one side, and that side can be subsequently coated with an aqueous polymeric system to form an adjacent water-borne biodegradable polymeric layer. The paper may be flattened via "sizing," which in the industry means that it can be coated with an aqueous polymeric suspension containing various inorganic fillers such as clays, calcium carbonate, titanium dioxide, methyl cellulose, silicon dioxide etc. The suspension can be dried, and the paper calendared to deliver a flatter surface than before sizing, as the inorganic fillers & binders dry down to fill in the porous rough surface of the paper.

Alternatively, the paper may be machine glazed during the paper manufacturing process via a mechanical ironing/pressing step that sometimes involves heat—in this case the paper fibers are squashed together and flattened in order to densify the paper surface and remove porosity.

In some cases, sizing and machine glazing can be combined to get an even flatter more perfect surface during paper manufacturing, before subsequently being coated with the water-borne biodegradable polymeric layers (e.g. front and back middle layers).

In other cases, a vellum or glassine or tracing paper might be used which are already naturally very flat—such papers are made by a process that during the manufacturing densifies the paper structure throughout its entire thickness process and further sizing or glazing is not required. Examples of papers suitable for biodegradable & recyclable paper layer making a biodegradable paper barrier laminate include Leine Nature® paper (grammage 85 g/m²) from Sappi®, a machine glazed paper certified "OK Home Compost"; NiklaSelect V Natural Linen paper (99 g/m²) from Birgl & Bergmeister, a paper sized on one side only; PackPro® 7.0 paper (65 g/m²) from Birgl & Bergmeister, a paper sized on both sides; Axello papers from BillerudKorsnás™ (including from Axello Tough White paper, 80 g/m²) which has been designed to be tougher than many other papers and so may have some advantages in the distribution chain; SCG Glassine® paper (58 g/m²) from SCG/Prepack. As shown in the Table 1 below, these papers pass the paper recycling protocols at both Western Michigan University in the USA and at the PTS Institute in Germany. These papers also pass the OECD 301B biodegradation test.

TABLE 1

| Paper Grade | Western Michigan Paper Recycling Protocol | PTS Paper Recycling Protocol | OECD 301B Biodegradation Test |
|---|---|---|---|
| Leine Nature ® 85 g/m² Sappi ® | PASS | PASS | PASS |
| NiklaSelect V Natural Linen 100 g/m² Birgl & Bergmeister | PASS | PASS | PASS |
| PackPro 7.0 80 g/m² Birgl & Bergmeister | PASS | PASS | PASS |
| Axello ® Tough White 80 g/m² BillerudKorsnäs | PASS | PASS | PASS |
| Glassine 58 g/m² SCG Packaging | PASSED internal SCG recycling protocols | PASSED internal SCG recycling protocols | PASS |

Other suitable papers could include paper especially prepared for subsequent decorative metallization, such as Nikkalett Spezial TD paper (60 g/m²) from Birgl & Bergmeister.

Front inner layer 14 and back inner layer 24 can comprise a polymeric layer including a water-soluble or a water-insoluble polymeric layer. The front and back inner layers can also be referred to as a biodegradable polymeric layer or polymeric layer. In some examples, front inner layer 14 and back inner layer 24 can comprise PVOH (polyvinyl alcohol), PBS (polybutylene succinate), PB SA (polybutylene succinate adipate), PHA (polyhydroxylalkonate), PVDC (polyvinylidene chloride), carnauba wax and/or a readily biodegradable TPS (thermo-plastic starch such as the Novamont™ Mater-BI®). The polymeric layer can include copolymers or derivatives suitable for use as a water-soluble polymeric layers selected from polyvinyl alcohol (PVOH), polyvinyl alcohol copolymers such as butenediol-vinyl alcohol copolymers (BVOH), which are produced by copolymerization of butenediol with vinyl acetate followed by the hydrolysis of vinyl acetate, suitable butenediol monomers being selected from 3,4-diol-1-butene, 3,4-diacyloxy-1-butenes, 3-acyloxy-4-ol-1-butenes, 4-acyloxy-3-ol-1-butenes and the like; polyvinyl pyrrolidone; polyalkylene oxides, such as polyethylene oxides or polyethylene glycols (PEG); poly(methacrylic acid), polyacrylic acids, polyacrylates, acrylate copolymers, maleic/acrylic acids copolymers; polyacrylamide; poly(2-acrylamido-2-methyl-1-propanesulfonic acid (polyAMPS); polyamides, poly-N-vinyl acetamide (PNVA); polycarboxylic acids and salts; cellulose derivatives such as cellulose ethers, methylcellulose, hydroxyethyl cellulose, carboxymethylcellulose; hydroxypropyl methylcellulose; natural gums such as xanthan and carrageenan gum; sodium alginates; maltodextrin, low molecular weight dextrin; sugars; polysaccharides; polyamino acids or peptides; proteins such as casein and/or caseinate (e.g. such as those commercialized by Lactips). In some examples the front and back inner layers can include water-soluble biodegradable polymers selected from the group consisting of polyvinyl alcohol, polyethylene oxide, methylcellulose, sodium alginate, and combinations thereof.

For applications where a "plastic free" product is desired, the majority component of the front and back middle layers can be a water-soluble, naturally derived polymer, such as sodium alginate.

The inner layers can include at least 60%, biodegradable, water-soluble polymer, alternatively at least 70%, and alternatively at least 80%. The polymer can have an average molecular weight (of about 1,000 Da to about 1,000,000 Da, or any integer value from about 1,000 Da to about 1,000,000 Da, or any range formed by any of the preceding values such as about 10,000 Da to about 300,000 Da, about 20,000 Da to about 150,000 Da, etc. More specifically polyvinyl alcohol could have a molecular weight in the range of 30,000-150,000 Da. Polyethylene oxide could have a molecular weight in the range of 50,000 Da to 400,000 Da. Methylcelluloses could have a molecular weight in the range 10,000 Da to 100,000 Da. If a homopolymer polyvinyl alcohol is used, the degree of hydrolysis could be 70-100%, or any integer value for percentage between 70% and 100%, or any range formed by any of these values, such as 80-100%, 85-100%, 90-100%, 95-100%, 98-100%, 99-100%, 85-99%, 90-99%, 95-99%, 98-99%, 80-98%, 85-98%, 90-98%, 95-98%, 80-95%, 85-95%, 90-95%, etc. In some examples, the biodegradable polymeric layer used as the lamination layer between the biodegradable paper layer and the biodegradable primer layer is water-borne because a thinner and flatter biodegradable polymeric layer can be formed than if the biodegradable polymeric layer was extrusion coated onto the surface of the biodegradable and recyclable paper layer (e.g. front and back middle layers). In some embodiments, the biodegradable polymeric layer can be used as a lamination layer between the biodegradable & recyclable paper layer and the biodegradable primer layer is soluble, since this increases the speed at which these two layers can separate in a typical paper repulping unit and hence will increase the likelihood of the entire structure being recyclable in the typical paper recycling stream. In some embodiments, the biodegradable polymeric layer can be used as the lamination layer between the biodegradable and recyclable paper layer and the biodegradable primer layer is both soluble and laid down from a water-borne composition because such a biodegradable polymer layer would be both very flat (to help maximize barrier properties of the entire structure) and also its soluble nature would minimize the time for the paper to break up in a typical paper repulping stream.

The biodegradable polymeric layers that are water-soluble may contain additional ingredients such disintegrants, plasticizers, surfactants, lubricants/release agents, fillers, extenders, antiblocking agents, detackifying agents, antifoams, or other functional ingredients. It may be required for certain applications that the biodegradable polymeric layers that are water-soluble contain disintegrants to increase their dissolution rate in water. Suitable disintegrants are, but are not limited to, corn/potato starch, methyl celluloses, mineral clay powders, croscarmellose (cross-linked cellulose), crospovidone (cross-linked polyvinyl N-pyrrolidone, or PVP), sodium starch glycolate (cross-linked starch). The water-soluble polymeric layers can comprise between 0.1% and 15%, and alternatively from about 1% to about 15% by weight of disintegrants. In some examples, the biodegradable polymeric layers that are water-soluble may contain water-soluble plasticizers. The water-soluble plasticizer can be selected from polyols, sugar alcohols, and mixtures thereof. Suitable polyols can include polyols selected from the group consisting of glycerol, diglycerol, ethylene glycol, diethylene glycol, triethylene glycol, tetraethylene glycol, polyethylene glycols up to 400 Da molecular weight, neopentyl glycol, 1,2-propylene glycol, 1,3-propanediol, dipropylene glycol, polypropylene glycol, 2-methyl-1,3-propanediol, methylene glycol, trimethylolpropane, hexylene glycol, neopentyl glycol, and polyether polyols, or a mixture thereof. Suitable sugar alcohols include sugar alcohols selected from the group consisting of isomalt, maltitol, sorbitol, xylitol, erythritol, adonitol, dulcitol, pentaerythritol and mannitol, or a mixture thereof. In some cases, the plasticizer could be selected from the following list: ethanolamine, alkyl citrate, isosorbide, pentaerythritol, glucosamine, N-methylglucamine or sodium cumene sulfonate. Less mobile plasticizers such as sorbitol or polyethylene oxide can facilitate the formation of water-soluble polymeric layers with greater barrier properties than water-soluble polymeric layers including a more mobile plasticizer such as glycerol. In some circumstances when there is a desire to use as many naturally derived materials as possible, the following plasticizers could also be used: vegetable oil, polysorbitol, dimethicone, mineral oil, paraffin, $C_1$-$C_3$ alcohols, dimethyl sulfoxide, N, N-dimethylacetamide, sucrose, corn syrup, fructose, dioctyl sodium-sulfosuccinate, triethyl citrate, tributyl citrate, 1,2-propylene glycol, mono, di- or triacetates of glycerin, natural gums, citrates, and mixtures thereof. Water-soluble plasticizers can be selected from glycerol, 1,2-propanediol, 20 dipropylene glycol, 2-methyl-1,3-propanediol, trimethylolpropane, triethylene glycol, polyethylene glycol, sorbitol, or a mixture thereof. In some examples, water-soluble plasticizers can be selected from glycerol, sorbitol, trimethylolpropane, dipropylene glycol, and mixtures thereof. The water-soluble polymeric layers can comprise between 5% and 50%, alternatively between 10% and 40%, and alternatively from about 12% to about 30% by weight of plasticizers. In some examples, the biodegradable polymeric layers can comprise a surfactant. Suitable surfactants may belong to the non-ionic, cationic, anionic or zwitterionic classes. Suitable surfactants are, but are not limited to, poloxamers (polyoxyethylene polyoxypropylene glycols), alcohol ethoxylates, alkylphenol ethoxylates, tertiary acetylenic glycols and alkanolamides (non-ionic), polyoxyethylene amines, quaternary ammonium salts and quaternized polyoxyethylene amines (cationic), and amine oxides, N-alkylbetaines and sulfobetaines (zwitterionic). Other suitable surfactants are dioctyl sodium sulfosuccinate, lactylated fatty acid esters of glycerol and propylene glycol, lactylic esters of fatty acids, sodium alkyl sulfates, polysorbate 20, polysorbate 60, polysorbate 65, polysorbate 80, lecithin, acetylated fatty acid esters of glycerol and propylene glycol, and acetylated esters of 5 fatty acids, and combinations thereof. The water-soluble polymeric layers can comprise between 0.1% and 2.5%, alternatively from about 1% to about 2% by weight of surfactants. In some examples, the biodegradable polymeric layers according to the disclosure can comprise lubricants/release agents. Suitable lubricants/release agents can include, but are not limited to, fatty acids and their salts, fatty alcohols, fatty esters, fatty amines, fatty amine acetates, fatty amides, and combinations thereof. In some examples, lubricants/release agents can be fatty acids, fatty acid salts, fatty amine acetates, and mixtures thereof. The water-soluble polymeric layers can comprise between 0.02% to 1.5%, and alternatively from about 0.1% to about 1% by weight of lubricants/release agents. The biodegradable polymeric layers can comprise fillers, extenders, anti-blocking agents, de-tackifying agents. Suitable fillers, extenders, anti-blocking agents, de-tackifying agents can include, but are not limited to, starches, modified starches, crosslinked polyvinylpyrrolidone, crosslinked cellulose, microcrystalline cellulose, silica, metallic oxides, calcium carbonate, talc, mica, and combinations thereof. In some examples, the biodegradable polymeric layers can comprise between 0.1% to 25%, alternatively from about 1% to about 15% by weight of fillers, extenders, anti-blocking agents, de-tackifying agents. In absence of starch, the biodegradable polymeric layers can comprise between 1% to 5% by weight of fillers, extenders, anti-blocking agents. In some examples, the water-borne biodegradable polymeric layers that are water-soluble can comprise antifoams. Suitable antifoams can include, but are not limited to, polydimethylsiloxanes and hydrocarbon blends. The water-soluble polymeric layers can comprise between 0.001% and 0.5%, alternatively from about 0.01% to about 0.1% by weight of antifoams. Biodegradable paper barrier laminates where at least one of the biodegradable polymeric layers can be made from a water-soluble polymer according to the invention may contain residual moisture in the water-soluble layer depending on the hygroscopy and the isotherm of the laminate components at given temperature and humidity conditions measured by Karl Fischer titration. For instance, water-soluble polyvinyl-alcohol layers in the laminate may contain about 4-8% residual moisture at 23° C. and 50% relative humidity.

In some embodiments at least one of the biodegradable front inner layer 14 and back inner layer 24 can be made from a water in-soluble polymer. These materials are commonly referred to as "bioplastics" as well as biodegradable polymers. Such a biodegradable polymeric layer could be suitable to form the lamination layer between the biodegradable and recyclable paper layer and the biodegradable primer layer—and/or could be used to form the heat seal layer of the biodegradable & recyclable paper barrier laminate.

In one instance, biodegradable aliphatic polyesters and copolyesters can be produced by large-scale bacterial fermentation. Collectively termed polyhydroxyalkanoates, also known as "PHAs", these polymers can be synthesized from plant or bacteria fed with a particular substrate, such as glucose, in a fermentation plant. In many instances, the structural or mechanical properties of PHAs can be customized to fit the specifications of the desired end product. PHAs and their copolymers can degrade both aerobically and anaerobically. This makes them particularly well suited for composting or rapidly and completely degrading in the environment. Such bioplastics are often sold in a form where the plastic is suspended in aqueous emulsions and can be dried into films on various substrates, although they can also be sold in pellet form for extrusion into films and coatings. The PHA can be obtained as copolymer dispersion coatings Danimer Scientific, Inc. produces poly(beta-hydroxyalkano-ate), poly(3-hydroxybutyrate-co-3-hydroxyhexanoate) NODAX™) and Kaneka produces poly(3-hydroxybutyrate-co-3-hydroxyhexanoate). Non-limiting examples of PHA copolymers include those described in U.S. Pat. No. 5,498,692. Other PHA copolymers can by synthesized by methods known to one skilled in the art, such as, from microorganisms, the ring-opening polymerization of beta-lactones, the dehydration-polycondensation of hydroxyalkanoic acid, and the dealcoholization-polycondensation of the alkyl ether of hydroxyalkanoic acid, as described in Volova, "Polyhydroxy Alkanoates Plastic Materials of the 21" Century: Production, Properties, and Application, Nova Science Publishers, Inc., (2004), incorporated herein by reference.

Other possible biodegradable water in-soluble polymers could include biodegradable thermoplastic material selected from the group consisting of aliphatic aromatic polyesters (e. g., ECOFLEX® from BASF), thermoplastic starches (e.g., MATER-BI from Novamont or PLANTIC® from Plantic/Kuraray), polybutylene succinate (PBS), polybutylene succinate adipate (PBSA) and copolymers thereof (e.g., BIONOLLE® from ShoWa High polymer Co. or PBSA from Mitsubishi Chemicals) and mixtures thereof. Although these polymers are not commonly sold in the water-borne form today, it is possible that such forms may be developed in the future.

In some examples, the biodegradable polymeric layer used as the lamination layer between the biodegradable paper layer and the biodegradable primer layer can be water-borne because a thinner and flatter biodegradable polymeric layer can be formed than if the biodegradable polymeric layer was extrusion coated onto the surface of the biodegradable paper layer. In some examples, the biodegradable polymeric layer can be used as the lamination layer between the biodegradable and recyclable paper layer and the biodegradable primer layer can be soluble, since this increases the speed at which these two layers can separate in a typical paper repulping unit and hence will increase the likelihood of the entire structure being recyclable in the typical paper recycling stream.

In some examples, a biodegradable adhesive layer can adhere an already formed biodegradable film to the rest of the laminate structure. Such an adhesive could be either a biodegradable solution-based or solvent-based adhesive composition. Nonlimiting examples of the biodegradable adhesive layer can include biodegradable polyvinyl acetates, starches, maltodextrins, natural waxes, artificial waxes and polyester-polyurethane blends. In some embodiments, the biodegradable adhesive layer could be a commercially available grade from BASF such as Epotal 3675 or Epotal 3702 or Epotal P100ECO, which are both biodegradable and compostable. In another embodiments, the adhesive could be BioTAK® by Berkshire Labels; or Bostik 43298 Thermogrip hotmelt adhesive. A soluble adhesive may have benefits to enhance recyclability in the typical paper repulping system, since it may accelerate the barrier paper structure to break up—it would bring similar advantages to the biodegradation process.

The sachet 1 according to the present invention can be opaque or translucent depending on the material selection. The sachet 1 can comprise a printed area. Printing may be achieved using standard printing techniques, such as flexographic, gravure, or inkjet printing. The branding and/or other package information associated with the product within the package can be applied on one of the surfaces of the sachets. In some embodiments, the printed area can be applied on the outer surface of the middle layer. Branding can include logos, trade names, trademarks, icons, and the like associated with the product within the package. Branding can be utilized to inform a consumer of the product within the package. Package information can include the size of the product, the number of products within the package, an exemplary image of the products contained within the package, recyclability logos, and the like associated with the products within the package. In all aspects of the invention, the ink that is deposited can be either solvent-based or water-based and the pigments within the ink may be either organic or inorganic, or a combination of both. In some embodiments, the ink is highly abrasion resistant. For example, the high abrasion resistant ink can include coatings cured by ultraviolet radiation (UV) or electron beams (EB). In some embodiments, any organic pigments within the ink are derived from a petroleum source. In some embodiments, any organic pigments within the ink are derived from a renewable resource, such as soy, a plant. In some embodiments, any organic pigments within the ink will also be biodegradable if the pigment is organic and designed to biodegrade. In other embodiments, any inorganic pigments within the ink will be made from an inorganic metal oxide that is safely dispersible and not harmful to the environment at the levels used, even if itself is not biodegradable. Non-limiting examples of inks that are not biodegradable but do not inhibit biodegradation and can safely disperse during biodegradation include ECO-SUREI™ from Gans Ink & Supply Co. and the solvent based VUTEk® and BioVu™ inks from EFI, which are derived completely from renewable resources (e.g., corn). Others include SunVisto® AquaGreen, SunSpectro® (Aquathene) from Sun Chemicals™; and also INXhrc™ and GENESIS™ GS from Sakata Inc. A biodegradable ink is not limited particularly and may for example be a regenerated vegetable oil ink, soybean oil ink and the like. The soybean oil ink is obtained by replacing all or a part of a petroleum-based solvent and a drying oil in a conventional ink with a soybean oil, and is advantageous since it allows the ink to be readily separated from the paper and to be degraded in a soil. The soybean oil ink may be available commercially for example from TOYO INK MFG. CO., LTD. or TOPPAN PRINTING CO., LTD. Another potential biodegradable ink is and Blue Iris from Sun Chemicals™. The ink is present in a thickness of about 0.5 µm to about 20 µm, alternative about 1 µm to about 10 µm, and alternatively from about 2.5 µm to about 3.5 µm. The biodegradable laminate of the present disclosure may comprise inks and/or dyes to provide a background color to the packages of the present disclosure. To further clarify the background color, it is worth noting that paper layers comprise a base color. A base color of the paper layer is the color of the package without inks or dyes. For example, bleached paper is white in color, unbleached is brown in color, grass-derived paper is green in color and paper which includes recycled content is grey in color. A background color is any color that is not a base color, e.g. blue, red, green, yellow, purple, orange, black, or combinations thereof. However, background color can also include white, brown, or grey, if the color is achieved via inks and/or dyes. In order to reduce the use of inks/dyes for the benefit of the recycling process, the natural color of the paper layer may be utilized. For example, inks/dyes may be used to define the background color of the consumer-facing panel only, whereas the natural color of the paper layer would be used as background color for the other panels of the flexible package.

Front outer layer 12 and back outer layer 22 can be from about 5 µm to about 50 µm thick, alternatively from about 10 µm to about 40 µm thick, and alternatively from about 20 µm to about 30 µm thick. The front middle layer 13 and back middle layer 23 can be from about 30 to about 120 gsm, alternatively from about 40 to about 110 gsm, alternatively from about 50 to about 100 gsm, and alternatively from about 60 to about 90 gsm. The front inner layer 14 and the back inner layer 24 can be from about 1 µm to about 150 µm thick, alternatively from about 2 µm to about 100 µm, alternatively from about 3 µm to about 40 µm thick, alternatively from about 5 µm to about 35 µm, and alternatively from about 10 µm to about 30 µm thick.

Figure 1C:
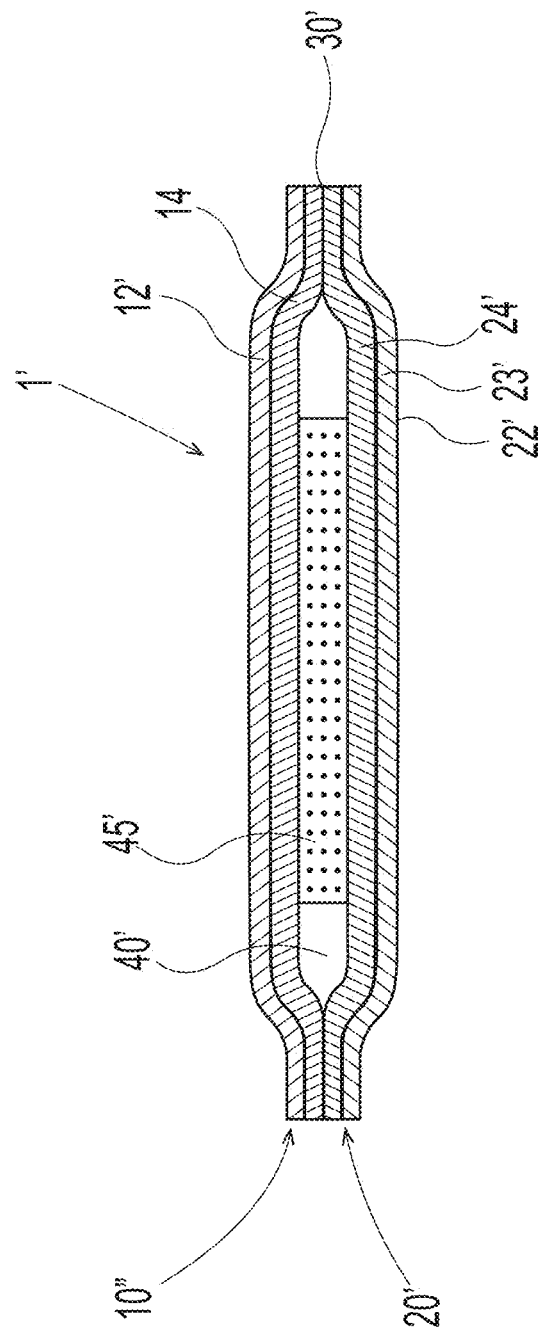
FIG. 1C is a cross-sectional view of a second sachet.

FIG. 1C is a cross-sectional view of sachet 1', this view is similar to FIG. 1B, which is taken along line 1B-1B. Sachet 1' would appear the same as the perspective view of sachet 1 in FIG. 1A. In this example, front film 10' and back film 20' are made from a multi-layer structure that can comprise two layers. Front film 10' and back film 20', and more specifically front inner layer 14' and back inner layer 24', can be permanently joined at heat seal 30' to form compartment 40', which is adapted for storing solid article 45'.

In this example, front film 10' can comprise front outer layer 12' and front inner layer 14' and back film 20' can comprise back outer layer 22' and back inner layer 24'. In one example, front outer layer 12' and back outer layer 22' can comprise cellulose, cellulose acetate or metalized cellulose, or metalized cellulose acetate and the front inner layer 14' and back inner layer 24' can comprise PVOH, PBS, PBSA, PHA, carnauba wax, a biodegradable TPS and/or PVDC (polyvinylidene chloride). In one example, the front outer layer 12' and back outer layer 22' comprise cellulose and the front inner layer 14' and back inner layer 24' comprise metalized PBSA. In one embodiment, the front outer layer 12' and back outer layer 22' comprise metalized cellulose and the front inner layer 14' and back inner layer 24' comprise PBSA. The sachet 1' can comprise a biodegradable adhesive layer between the outer and inner layers similar to what described for the sachet 1.

The sachet 1' can be either opaque or translucent or transparent depending on the cellulose type selected. For example, the cellulose can be transparent, having a metallic finish, translucent matte or white. The sachet 1 can comprise a printed area. Printing may be achieved using standard printing techniques, such as flexographic, gravure, or inkjet printing. The branding and/or other package information associated with the product within the package can be applied on one of the surfaces of the sachets. In some embodiments, the print is applied on a transparent or translucent cellulose outer layer on the surface facing the inner layers. This arrangement is particularly advantageous to protect the print from the environment or any damage from handling. In other embodiments, the print is applied directly on top of the outer layers. The ink application and type are similar to what already described for the sachet 1.

Front outer layer 12' and back outer layer 22' can be from about 5 µm to about 50 µm thick, alternatively from about 10 µm to about 30 µm thick, and alternatively from about 15 µm to about 25 µm thick. The front inner layer 14' and the back inner layer 24' can be from about 0.5 µm to about 100 µm thick, alternatively 1 µm to about 30 µm thick, and alternatively from about 1 µm to about 5 µm thick. Alternatively, the front inner layer 14' and the back inner layer 24' can be from about 1 µm to about 50 µm thick, alternatively from about 3 µm to about 40 µm thick, alternatively from about 5 µm to about 35 µm, and alternatively from about 10 µm to about 30 µm thick.

In some embodiments, there could be additional inorganic barrier layers to decrease the moisture transmission rate of the entire structure. The inorganic barrier layers can be disposed in any suitable portion in the front and or back film, including, but not limited to, the inner surface, outer surface, adjacent to the paper layer, adjacent to the polymeric layer, etc. Suitable inorganic coatings can be formed by vapor deposition of metals including but not limited to aluminum, magnesium, titanium, tin, indium, silicon, carbon, gold, silver, chromium, zinc, copper, cerium, hafnium, tantalum and diamond-like carbon. In certain embodiments, suitable inorganic coatings can be formed by vapor deposition of metal oxides, metal nitrides and related compounds. As used herein, metal oxides include aluminum oxides (e.g. $Al_2O_3$), aluminum carbide, aluminum nitride, magnesium oxide, titanium oxides (such as titanium dioxide, titanium(3) oxide or titanium monoxide), zinc oxide, tin oxide, yttrium oxide, or zirconium oxides (e.g. zirconium monoxide), calcium oxide, boron oxide or metalloid oxides such as silicon oxides, silicon oxycarbides, and silicon nitrides. Silicon oxide or nitride-based coatings could also be one selected from the group consisting of SiOX (where x is an integer of 1-4) or SiOXNY (where each of x and y is an integer of 1-3). The barrier layer can be a single component vapor deposition layer comprising at least one selected from the group above, or a dual component vapor deposition layer comprising at least one combination of two components selected from the group consisting of SiOx/Al2O3, SiO/ZnO, SiO/CaO, SiO/B2O3 and CaO/Ca(OH)2. The inorganic barrier coating layer can have a thickness of 5-1,000 nm, alternatively 20-500 nm, and alternatively 50-200 nm.

Some examples can also use a biodegradable primer layer together with the inorganic barrier layer. The role of the biodegradable primer layer is to flatten the surface of the paper-based structure that will be coated with the primer, as much as possible, before the inorganic barrier layer is deposited onto it. Therefore, the smaller the flatness value, the greater the barrier property is increased. It also needs to be suitable for the inorganic barrier layer to adhere to as well as possible, in order to form a strong interface to enable a stable barrier layer and to avoid delamination of the inorganic barrier layer from the underlying structure. In some cases, such a primer layer may be used only on top of the inorganic barrier layer, to prevent mechanical damage or oxidation and in this case may then be called a protective layer. A primer may also be used to provide additional heat resistance for the thermal hysteresis often experienced during a vapor deposition. A biodegradable primer layer may also sometimes be called a biodegradable lacquer or a biodegradable varnish, in addition to a protective layer. Whichever word is used to describe this layer, the purpose is the same. In some embodiments, the primer can be an inorganic-organic hybrid-polymer such as bio-ORMOCER® or ORMOCER® developed by The Fraunhofer Institute for Silicate Research in Wurzburg, Germany. These materials are a hybrid between a glass and a polymer, and the exact chemistry of these materials can be tailored to specific applications. ORMOCER® materials are synthesized via the sol-gel process and have strong covalent bonds between the inorganic and the organic moieties. The ratio of the inorganic to organic moieties can be altered to optimize properties for a specific application. Controlled hydrolysis and condensation reactions of organo-alkoxysilanes and metal alkoxides produce the inorganic network of the hybrid polymer ORMOCER®. The organic network forms via subsequent polymerization of reactive organic groups, which are introduced via the organo-alkoxysilanes. Typically, this involves epoxide polymerization or radical polymerization of acrylates or meth-acrylates for the non-biodegradable version. The organic network formation and hence the curing of the material can be induced by heat or UV light (e.g. Bio-ORMOCER®). Typically, to make bio-ORMOCER®, ORMOCER® is modified by either the biodegradable polymer chitosan or polycaprolactone, in order to make the biodegradable version, forming biodegradable functional groups for covalent coupling to the inorganic ORMOCER® network. In order to guarantee incorporation of the biodegradable components into the hybrid polymer network, some of these components are subjected to chemical modification. For example, the polycaprolactone derivative can be functionalized with tri-ethoxy-silane groups, in order to subsequently allow attachment of these biodegradable components to the inorganic network via hydrolysis and condensation reactions. For the polycaprolactone version, attachment of biodegradable precursors to the organic network of the hybrid material was achieved by functionalization with epoxy groups. The reactive epoxy groups subsequently participated in the polymerization reactions for formation of the organic network. In contrast, chitosan required no modification because it can link with the organic network via some of its own amino groups. The chitosan version tends to biodegrade at a faster rate. The polycaprolactone version was specifically designed with a moisture-triggered antimicrobial effect. Non-limiting examples of ORMOCER® and bio-ORMOCER® include those described in US. Pat. No. 2011/0250441 A1 and U.S. Pat. No. 6,709,757B2, in addition to German patents DE-OS 3828098 and DE4303570. Alternative embodiments to an inorganic-organic hybrid material could include, but are not limited to, a PVOH lacquer from the Huber Group in Germany or a shellac lacquer. Both these alternative options would also be expected to biodegrade. Typically, any primer layer would be laid down in such a way as to give a final cured thickness in the range 0.5-20 µm, alternatively 2-10 µm, and alternatively from 1-5 µm. It is important to keep this layer as thin as possible, to keep a good balance between protecting the barrier properties of the inorganic barrier layer—but also to prevent issues in the paper recycling stream. If the primer layer is too thick or too difficult to break up, it may clog up the filters in the paper re-pulping unit or cause optical defects in the resulting recycled paper.

It was surprisingly found that if the solid article was an open cell foam (OCF) article, like the example article in Table 3, and described hereafter, could be stored in a biodegradable and/or home compostable sachet. However, an article that was made from spun fibers, as described in Table 2 and made according to the method described in US Pub. No. 2019/0282461, cannot be stored in a biodegradable and/or home compostable sachet.

TABLE 2

Fibrous Article (Spun Fiber Shampoo)

| | % by mass of fibrous article |
|---|---|
| USP Water | 3.13 |
| Guar hydroxypropyltrimonium chloride[1] | 0.81 |
| Polyquaternium-76[2] | 0.16 |
| Polyvinyl alcohol[3] | 10.27 |
| Polyvinyl alcohol[4] | 10.27 |
| Citric Acid | 8.48 |
| Lauryl hydroxysultaine[5] | 12.16 |
| Sodium Laureth 1 Sulfate | 19.03 |
| Sodium Laureth-3 Sulfate | 2.59 |
| Sodium Undecyl Sulfate | 11.60 |
| Sodium Bicarbonate | 8.83 |
| Amodimethicone[6] | 4.63-9.26 |
| Fragrance and other minors | Q.S. |

[1]Jaguar® C500 supplied by Solvay®
[2]Mirapol® AM-T supplied by Solvay®
[3]Poval™ 3-80[3], PVA420H supplied by Kuraray®
[4]Poval™ 32-80 (420H), PVA403 supplied by Kuraray®
[5]Mackham® LHS supplied by Solvay®
[6]Y-14945 Amino Fluid supplied by Momentive®

TABLE 3

OCF Article (OCF Shampoo)

| | % by mass of solid article (article stored at ambient temperature and 40% RH) |
|---|---|
| USP Water | 8.53 |
| Glycerin | 8.80 |
| Guar hydroxypropyltrimonium chloride[1] | 1.09 |
| Polyvinyl alcohol[2] | 23.09 |
| Citric Acid | 2.01 |
| Sodium Lauroamphoacetate[3] | 10.86 |
| Sodium Lauryl Sulfate | 35.55 |

TABLE 3-continued

OCF Article (OCF Shampoo)

| | % by mass of solid article (article stored at ambient temperature and 40% RH) |
|---|---|
| Sodium Laureth-3 Sulfate | 9.64 |
| Sodium Benzoate | 0.43 |

[1]Jaguar ® C500 supplied by Solvay ®
[2]Selvol ™ Polyvinyl Alcohol 523 supplied by Sekisui Specialty Chemicals ®
[3]Miranol ® Ultra L 32 E by Solvay ®

Figures 2A, 2B:
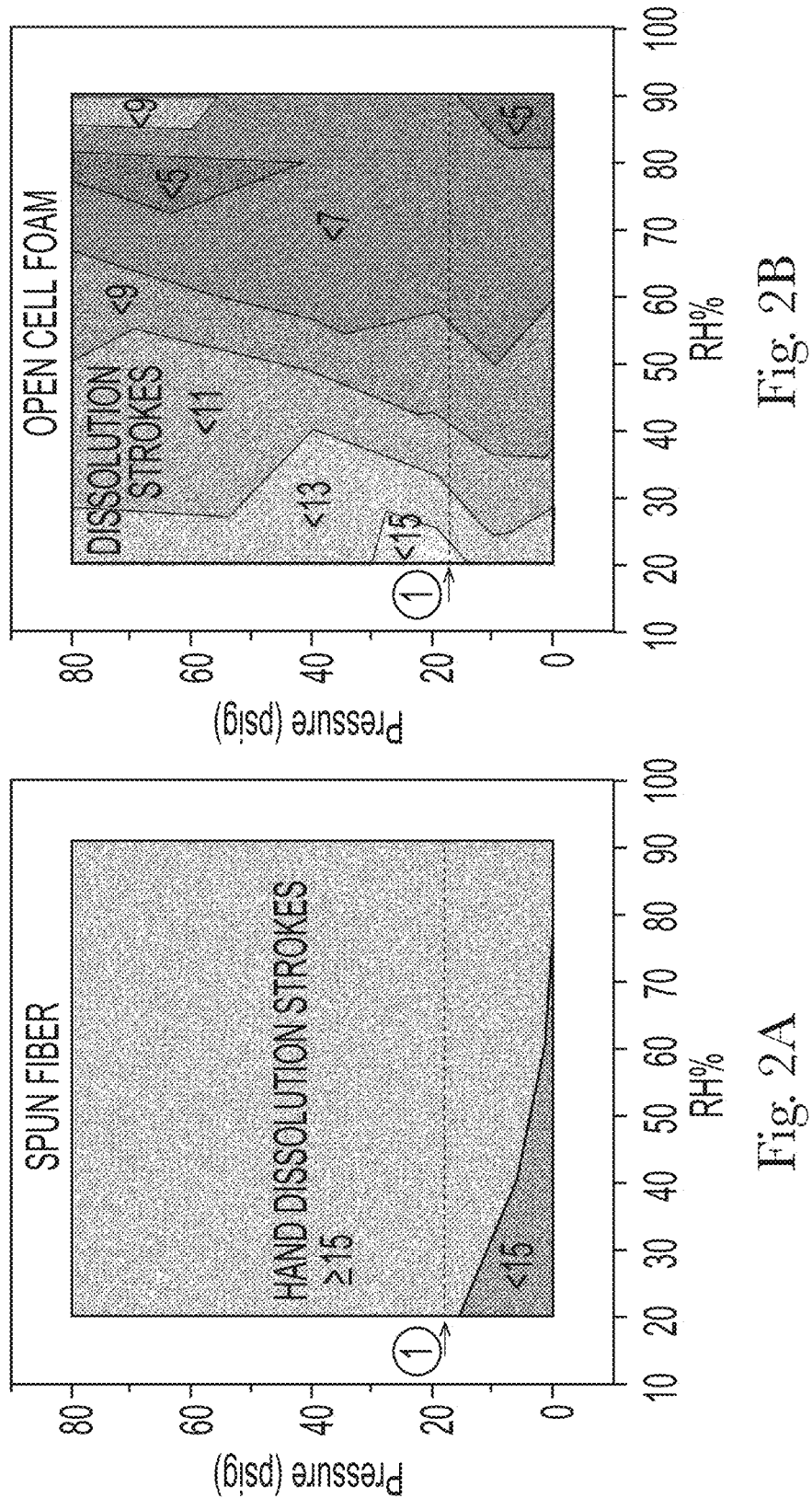
FIG. 2A shows the relative impact of compressive pressure and relative humidity to the dissolution of a Fibrous Article.
FIG. 2B shows the relative impact of compressive pressure and relative humidity to dissolution of an Open Cell Foam Article.

FIGS. 2A and 2B shows the relative impact of compressive pressure and relative humidity to article dissolution, as determined by the Hand Dissolution Method, described hereafter, for the Fibrous Article (Table 2) and OCF Article (Table 3), respectively. The articles were conditioned at 25° C. without any packaging to a set relative humidity (RH) for at least 48 hours, then subjected to a set compressive load for 15 seconds, then left to recover in the same set RH room for at least 48 hours and then assessed for appearance and hand dissolution according to the Hand Dissolution Test, described hereafter. The article was considered to have acceptable hand dissolution if the article required less than 15 strokes to dissolve. OCF and fibrous articles were tested at the following relative humidity combinations: 20%, 40%, 60%, 80%, 90% and pressure conditions: 0, 20, 40, 60, 80 psig for a total of 25 conditions. Three articles were tested for each condition. In FIGS. 2A and 2B dashed line 1 represents the typical compressive stress measured on a sachet during distribution and consumer handling.

As shown in FIG. 2A, it was found that the spun fiber had an unacceptable hand dissolution (greater than or equal to 15 strokes) for most relative humidity/pressure combinations, including 20 psig (137.9 kPa) and 80% relative humidity. It was found that for fibrous articles, even small amounts of compressive load at any relative humidity caused some level of irreversible deformation to the article.

However, as shown in FIG. 2B, the open cell foam had an acceptable hand dissolution (less than 15 strokes) across most of the relative humidity and pressure combinations, including 20 psig (137.9 kPa) and 90% relative humidity where the average hand dissolution is about 7. Furthermore, it was found that upon application of compressive loads, the OCF articles were found to fully recover their shape from 20 to 80% RH. OCF articles stored at 90% RH only partially recovered their initial shape after compression and thus were found to dissolve more slowly although still consumer acceptable.

While not willing to be bound by theory, it is believed that the structure of an OCF article can make it a preferable solid article for storage in biodegradable and/or home compostable sachets. FIG. 3A shows a micro-CT scan of a portion of an OCF article and FIG. 3B shows a micro-CT scan of a portion of a fibrous article. As shown in FIG. 3A, OCF articles have a relatively large average strut diameter (e.g. 30-50 µm), relative to other solid forms like fibrous articles. This increases the article robustness to humidity and even moist fingers, while still providing consumer acceptable dissolution. Furthermore, unlike articles with spun fibers, as shown in FIG. 3B, where individual fibers are randomly laid against one another, FIG. 3A shows the OCF struts are organized as a single integral piece with each strut being continually pushed in opposite directions from one another.

Solid Article

Solid articles can include, but are not limited to open cell foam articles, as described in U.S. Pat. Nos. 8,349,786, 8,461,091, and 8,349,787 and US Pub. No. 2012/0270029 and fibrous articles, as described in U.S. Pub. Nos. 2012/052036, 2018/0333339, and 2019/0282461, U.S. application Ser. No. 15/981,096, U.S. Pat. No. 9,545,364, incorporated by reference.

Open Cell Foam (OCF) Article

The OCF article can be an article that comprises a flexible, porous, dissolvable solid sheet. The OCF article can comprise a water-soluble polymer, wherein said solid sheet OCF article can have (i) a thickness ranging from about 0.5 mm to about 4 mm, alternatively from about 0.6 mm to about 3.5 mm, alternatively from about 0.7 mm to about 3 mm, alternatively from about 0.8 mm to about 2 mm, alternatively from about 1 mm to about 1.5 mm, as measured using Test 6 described hereinafter; and (ii) a Percent Open Cell Content of from about 80% to 100%, alternatively from about 85% to 100%, alternatively from about 90% to 100%, as measured by the Test 3 hereinafter; and (iii) an Overall Average Pore Size of from about 100 µm to about 2000 µm, alternatively from about 150 µm to about 1000 µm, alternatively from about 200 µm to about 600 µm, as measured by the Micro-CT method described in Test 2 hereinafter;

wherein said solid sheet OCF article has opposing top and bottom surfaces, said top surface having a Surface Average Pore Diameter that is greater than about 100 µm, alternatively greater than about 110 µm, alternatively greater than about 120 µm, alternatively greater than about 130 µm, most alternatively greater than about 150 µm as measured by the SEM method described in Test 1 hereinafter;

wherein said solid sheet OCF article comprises a top region adjacent to the top surface, a bottom region adjacent to the bottom surface, and a middle region therebetween; wherein said top, middle, and bottom regions have the same thickness, and each of said top, middle and bottom regions is characterized by an Average Pore Size; and wherein the ratio of Average Pore Size in said bottom region over that in said top region is from about 0.6 to about 1.5, alternatively from about 0.7 to about 1.4, alternatively from about 0.8 to about 1.3, most alternatively from about 1 to about 1.2.

Still further, the relative standard deviation (RSTD) between Average Pore Sizes in the top, middle and bottom regions of the article can be no more than 20%, alternatively no more than 15%, alternatively no more than 10%, most alternatively no more than 5%.

The article can have Average Cell Wall Thickness of from about 5 µm to about 200 µm, alternatively from about 10 µm to about 100 µm, alternatively from about 10 µm to about 80 µm, as measured by Test 2 hereinafter.

The article may contain a small amount of water. It can have a final moisture content of from about 0.5% to about 25%, alternatively from about 1% to about 20%, alternatively from about 3% to about 10%, by weight of said solid sheet OCF article, as measured by Test 4 hereinafter. An appropriate final moisture content in the resulting solid sheet OCF article may ensure the desired flexibility/deformability of the sheet article, as well as providing soft/smooth sensory feel to the consumers. If the final moisture content is too low, the sheet article may be too brittle or rigid. If the final moisture content is too high, the sheet article may be too sticky, and its overall structural integrity may be compromised.

The OCF article may comprise a basis weight of from about 50 grams/m$^2$ to about 250 grams/m$^2$, alternatively from about 80 grams/m$^2$ to about 220 grams/m$^2$, alternatively from about 100 grams/m$^2$ to about 200 grams/m$^2$, as measured by Test 6 described hereinafter.

The OCF article may have a density ranging from about 0.05 grams/cm$^3$ to about 0.5 grams/cm$^3$, alternatively from about 0.06 grams/cm$^3$ to about 0.4 grams/cm$^3$, alternatively from about 0.07 grams/cm$^3$ to about 0.2 grams/cm$^3$, alternatively from about 0.08 grams/cm$^3$ to about 0.15 grams/cm$^3$, as measured by Test 7 hereinafter. Density of the solid sheet OCF article can be lower than that of the sheet of aerated wet pre-mixture, also due to pore expansion that in turn leads to overall volume expansion.

Furthermore, the OCF article can be characterized by a Specific Surface Area of from about 0.03 m$^2$/g to about 0.25 m$^2$/g, alternatively from about 0.04 m$^2$/g to about 0.22 m$^2$/g, alternatively from 0.05 m$^2$/g to 0.2 m$^2$/g, alternatively from 0.1 m$^2$/g to 0.18 m$^2$/g, as measured by Test 8 described hereinafter. The Specific Surface Area of the solid sheet OCF article may be indicative of its porosity and may impact its dissolution rate, e.g., the greater the Specific Surface Area, the more porous the sheet article and the faster its dissolution rate.

Formulation

Water Soluble Polymer

The wet pre-mixture may comprise from about 3% to about 20% by weight of the pre-mixture of water-soluble polymer, alternatively from about 5% to about 15% by weight of the pre-mixture of water-soluble polymer, alternatively from about 7% to about 10% by weight of the pre-mixture of water soluble polymer.

After drying, the water-soluble polymer in the OCF article can be from about 10% to about 40%, alternatively from about 15% to about 30%, alternatively from about 20% to about 25%, by total weight of the solid sheet OCF article. In an example, the total amount of water-soluble polymer(s) OCF article can be less than or equal to 25% by total weight of such article.

Water-soluble polymers may be selected those with weight average molecular weights ranging from about 50,000 to about 400,000 Daltons, alternatively from about 60,000 to about 300,000 Daltons, alternatively from about 70,000 to about 200,000 Daltons, alternatively from about 80,000 to about 150,000 Daltons. The weight average molecular weight is computed by summing the average molecular weights of each polymer raw material multiplied by their respective relative weight percentages by weight of the total weight of polymers present within the porous solid. The weight average molecular weight of the water-soluble polymer used herein may impact the viscosity of the wet pre-mixture, which may in turn influence the bubble number and size during the aeration step as well as the pore expansion/opening results during the drying step. Further, the weight average molecular weight of the water-soluble polymer may affect the overall film-forming properties of the wet pre-mixture and its compatibility/incompatibility with certain surfactants.

The water-soluble polymers may include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymers may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers can also be used as water-soluble polymers. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

The water-soluble polymer may include starch. As used herein, the term "starch" include both naturally occurring or modified starches. Typical natural sources for starches can include cereals, tubers, roots, legumes and fruits. More specific natural sources can include corn, pea, potato, banana, barley, wheat, rice, sago, amaranth, tapioca, arrowroot, canna, sorghum, and waxy or high amylase varieties thereof. The natural starches can be modified by any modification method known in the art to form modified starches, including physically modified starches, such as sheared starches or thermally-inhibited starches; chemically modified starches, such as those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

In one example, water-soluble polymers may include polyvinyl alcohols, polyvinylpyrrolidones, polyalkylene oxides, starch and starch derivatives, pullulan, gelatin, hydroxypropylmethylcelluloses, methycelluloses, and carboxymethycelluloses. In another example, water-soluble polymers may include polyvinyl alcohols, and hydroxypropylmethylcelluloses.

Water-soluble polymers of the present invention can include polyvinyl alcohols characterized by a degree of hydrolysis ranging from about 40% to about 100%, alternatively from about 50% to about 95%, alternatively from about 70% to about 92%, alternatively from about 80% to about 90%. Commercially available polyvinyl alcohols include those from Celanese Corporation (Texas, USA)

under the CELVOL trade name including, but not limited to, CELVOL 523, CELVOL 530, CELVOL 540, CELVOL 518, CELVOL 513, CELVOL 508, CELVOL 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China); and combinations thereof. The flexible, porous, dissolvable solid sheet OCF article can comprise from about 10% to about 25%, alternatively from about 15% to about 23%, by total weight of such article, of a polyvinyl alcohol having a weight average molecular weight ranging from 80,000 to about 150,000 Daltons and a degree of hydrolysis ranging from about 80% to about 90%.

In addition to polyvinyl alcohols as mentioned hereinabove, a single starch or a combination of starches may be used as a filler material in such an amount as to reduce the overall level of water-soluble polymers required, so long as it helps provide the solid sheet OCF article with the requisite structure and physical/chemical characteristics as described herein. However, too much starch may comprise the solubility and structural integrity of the sheet article. Therefore, it can be desired that the solid sheet OCF article comprises no more than 20%, alternatively from 0% to 10%, alternatively from 0% to 5%, alternatively from 0% to 1%, by weight of said solid sheet OCF article, of starch.

Surfactants

In addition to the water-soluble polymer described hereinabove, the solid sheet OCF article can comprise one or more surfactants. The surfactants may function as emulsifying agents during the aeration process to create a sufficient amount of stable bubbles for forming the desired OCF structure of the article. Further, the surfactants may function as active ingredients for delivering a desired cleansing benefit.

The solid sheet OCF article comprises one or more surfactants selected from the group consisting of anionic surfactants, nonionic surfactants, cationic surfactants, zwitterionic surfactants, amphoteric surfactants, polymeric surfactants or combinations thereof. Depending on the desired application of such solid sheet OCF article and the desired consumer benefit to be achieved, different surfactants can be selected. One benefit can be that the OCF structures of the solid sheet OCF article allow for incorporation of a high surfactant content while still providing fast dissolution. Consequently, highly concentrated cleansing compositions can be formulated into the solid sheet OCF articles to provide a new and superior cleansing experience to the consumers.

The surfactant as used herein may include both surfactants from the conventional sense (i.e., those providing a consumer-noticeable lathering effect) and emulsifiers (i.e., those that do not provide any lathering performance but are intended primarily as a process aid in making a stable foam structure). Examples of emulsifiers for use as a surfactant component herein include mono- and di-glycerides, fatty alcohols, polyglycerol esters, propylene glycol esters, sorbitan esters and other emulsifiers known or otherwise commonly used to stabilize air interfaces.

The total amount of surfactants present in the solid sheet OCF article may range widely from about 5% to about 80%, alternatively from about 10% to about 70%, alternatively from about 30% to about 65%, by total weight of said solid sheet OCF article. Correspondingly, the wet pre-mixture may comprise from about 1% to about 40% by weight of the wet pre-mixture of surfactant(s), in one embodiment from about 2% to about 35% by weight of the wet pre-mixture of surfactant(s), in one embodiment from about 5% to about 30% by weight of the wet pre-mixture of surfactant(s).

The solid sheet OCF article can be a cleansing product containing from about 30% to about 80%, alternatively from about 40% to about 70%, alternatively from about 50% to about 65%, of one or more surfactants by total weight of said solid sheet OCF article. In such cases, the wet pre-mixture may comprise from about 10% to about 40% by weight of the wet pre-mixture of surfactant(s), in one embodiment from about 12% to about 35% by weight of the wet pre-mixture of surfactant(s), in one embodiment from about 15% to about 30% by weight of the wet pre-mixture of surfactant(s).

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

One category of anionic surfactants particularly can include $C_6$-$C_{20}$ linear alkylbenzene sulphonate (LAS) surfactant. LAS surfactants are well known in the art and can be readily obtained by sulfonating commercially available linear alkylbenzenes. Exemplary $C_{10}$-$C_{20}$ linear alkylbenzene sulfonates that can be used can include alkali metal, alkaline earth metal or ammonium salts of $C_{10}$-$C_{20}$ linear alkylbenzene sulfonic acids, and alternatively the sodium, potassium, magnesium and/or ammonium salts of $C_{11}$-$C_{18}$ or $C_{11}$-$C_{14}$ linear alkylbenzene sulfonic acids. In one example, the sodium or potassium salts of $C_{12}$ and/or $C_{14}$ linear alkylbenzene sulfonic acids, and alternatively is the sodium salt of $C_{12}$ and/or $C_{14}$ linear alkylbenzene sulfonic acid, i.e., sodium dodecylbenzene sulfonate or sodium tetradecylbenzene sulfonate.

LAS provides superior cleaning benefit and is especially suitable for use in laundry detergent applications. It has been found that when polyvinyl alcohol having a higher weight average molecular weight (e.g., from about 50,000 to about 400,000 Daltons, alternatively from about 60,000 to about 300,000 Daltons, alternatively from about 70,000 to about 200,000 Daltons, most alternatively from about 80,000 to about 150,000 Daltons) is used as the film-former and carrier, LAS can be used as a major surfactant, i.e., present in an amount that is more than 50% by weight of the total surfactant content in the solid sheet OCF article, without adversely affecting the film-forming performance and stability of the overall composition. Correspondingly, in one example, LAS is used as the major surfactant in the solid sheet OCF article. If present, the amount of LAS in the solid sheet OCF article may range from about 10% to about 70%, alternatively from about 20% to about 65%, alternatively from about 40% to about 60%, by total weight of the solid sheet OCF article.

Another category of anionic surfactants can include sodium trideceth sulfates (STS) having a weight average degree of alkoxylation ranging from about 0.5 to about 5, alternatively from about 0.8 to about 4, alternatively from about 1 to about 3, most alternatively from about 1.5 to about 2.5. Trideceth is a 13-carbon branched alkoxylated hydrocarbon comprising, in one embodiment, an average of at least 1 methyl branch per molecule. STS may include ST(EOxPOy)S, while EOx refers to repeating ethylene oxide units with a repeating number x ranging from 0 to 5, alternatively from 1 to 4, alternatively from 1 to 3, and while POy refers to repeating propylene oxide units with a repeating number y ranging from 0 to 5, alternatively from 0 to 4, alternatively from 0 to 2. It is understood that a material such as ST2S with a weight average degree of ethoxylation of about 2, for example, may comprise a significant amount of molecules which have no ethoxylate, 1 mole ethoxylate, 3 mole ethoxylate, and so on, while the distribution of ethoxylation can be broad, narrow or truncated, which still results in an overall weight average degree of ethoxylation of about 2. STS is particularly suitable for personal cleansing applications, and it has been found that when polyvinyl alcohol having a higher weight average molecular weight (e.g., from about 50,000 to about 400,000 Daltons, alternatively from about 60,000 to about 300,000 Daltons, alternatively from about 70,000 to about 200,000 Daltons, most alternatively from about 80,000 to about 150,000 Daltons) is used as the film-former and carrier, STS can be used as a major surfactant, i.e., present in an amount that is more than 50% by weight of the total surfactant content in the solid sheet OCF article, without adversely affecting the film-forming performance and stability of the overall composition. Correspondingly, STS can be used as the major surfactant in the solid sheet OCF article. If present, the amount of STS in the solid sheet OCF article may range from about 10% to about 70%, alternatively from about 20% to about 65%, alternatively from about 40% to about 60%, by total weight of the solid sheet OCF article.

Another category of suitable anionic surfactants can include alkyl sulfates. These materials have the respective formulae $ROSO_3M$, wherein R is alkyl or alkenyl of from about 6 to about 20 carbon atoms, x is 1 to 10, and M is a water-soluble cation such as ammonium, sodium, potassium and triethanolamine. Alternatively, R has from about 6 to about 18, alternatively from about 8 to about 16, alternatively from about 10 to about 14, carbon atoms. It has been found that when polyvinyl alcohol having a higher weight average molecular weight (e.g., from about 50,000 to about 400,000 Daltons, alternatively from about 60,000 to about 300,000 Daltons, alternatively from about 70,000 to about 200,000 Daltons, most alternatively from about 80,000 to about 150,000 Daltons) is used as the film-former and carrier, other surfactants, such as LAS and/or STS, can be used as the major surfactant in the solid sheet OCF article, without adversely affecting the film-forming performance and stability of the overall composition. Therefore, it can be desirable to provide a solid sheet OCF article with no more than about 20%, alternatively from 0% to about 10%, alternatively from 0% to about 5%, most alternatively from 0% to about 1%, by weight of said solid sheet OCF article, of AS.

Another category of suitable anionic surfactants can include $C_6$-$C_{20}$ linear or branched alkylalkoxy sulfates (AAS). Among this category, linear or branched alkylethoxy sulfates (AES) having the respective formulae $RO(C_2H_4O)_xSO_3M$ can be included, wherein R is alkyl or alkenyl of from about 6 to about 20 carbon atoms, x is 1 to 10, and M is a water-soluble cation such as ammonium, sodium, potassium and triethanolamine. Alternatively, R has from about 6 to about 18, alternatively from about 8 to about 16, alternatively from about 10 to about 14, carbon atoms. The AES surfactants are typically made as condensation products of ethylene oxide and monohydric alcohol's having from about 6 to about 20 carbon atoms. Useful alcohols can be derived from fats, e.g., coconut oil or tallow, or can be synthetic. Lauryl alcohol and straight chain alcohol's derived from coconut oil can be used. Such alcohol's are reacted with about 1 to about 10, alternatively from about 3 to about 5, and especially about 3, molar proportions of ethylene oxide and the resulting mixture of molecular species having, for example, an average of 3 moles of ethylene oxide per mole of alcohol, is sulfated and neutralized. AES are those comprising a mixture of individual compounds, said mixture having an average alkyl chain length of from about 10 to about 16 carbon atoms and an average degree of ethoxylation of from about 1 to about 4 moles of ethylene oxide. If present, the amount of AAS in the solid sheet OCF article may range from about 2% to about 40%, alternatively from about 5% to about 30%, alternatively from about 8% to about 12%, by total weight of the solid sheet OCF article.

Other suitable anionic surfactants include water-soluble salts of the organic, sulfuric acid reaction products of the general formula $[R^1$—$SO_3$-$M]$, wherein $R^1$ is chosen from the group consisting of a straight or branched chain, saturated aliphatic hydrocarbon radical having from about 6 to about 20, alternatively about 10 to about 18, carbon atoms; and M is a cation. In some examples, alkali metal and ammonium sulfonated $C_{10\text{-}18}$ n-paraffins can be included. Other suitable anionic surfactants include olefin sulfonates having about 12 to about 24 carbon atoms. The α-olefins from which the olefin sulfonates are derived are mono-olefins having about 12 to about 24 carbon atoms, alternatively about 14 to about 16 carbon atoms. Alternatively, they are straight chain olefins.

Another class of anionic surfactants suitable for use in the fabric and home care compositions is the β-alkyloxy alkane sulfonates. These compounds have the following formula:

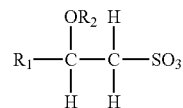

where $R_1$ is a straight chain alkyl group having from about 6 to about 20 carbon atoms, $R_2$ is a lower alkyl group having from about 1 to about 3 carbon atoms, and M is a water-soluble cation as hereinbefore described.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Still other suitable anionic surfactants are the succinamates, examples of which include disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Nonionic surfactants that can be included into the solid sheet OCF article may be any conventional nonionic surfactants, including but not limited to: alkyl alkoxylated alcohols, alkyl alkoxylated phenols, alkyl polysaccharides (especially alkyl glucosides and alkyl polyglucosides), polyhydroxy fatty acid amides, alkoxylated fatty acid esters, sucrose esters, sorbitan esters and alkoxylated derivatives of sorbitan esters, amine oxides, and the like. Nonionic surfactants can include those of the formula $R^1(OC_2H_4)$—$OH$, wherein $R^1$ is a $C_8$-$C_{18}$ alkyl group or alkyl phenyl group, and n is from about 1 to about 80. In some examples, $C_8$-$C_{18}$ alkyl ethoxylated alcohols having a weight average degree of ethoxylation from about 1 to about 20, alternatively from about 5 to about 15, alternatively from about 7 to about 10, such as NEODOL® nonionic surfactants commercially available from Shell® are included. Other non-limiting examples of nonionic surfactants useful herein include: $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols (BA); $C_{14}$-$C_{22}$ mid-chain branched alkyl alkoxylates, $BAE_x$, wherein x is from 1 to 30; alkyl polysaccharides, specifically alkyl polyglycosides; Polyhydroxy fatty acid amides; and ether capped poly(oxyalkylated) alcohol surfactants. Suitable nonionic surfactants also include those sold under the tradename Lutensol® from BASF.

The nonionic surfactant can be selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

The surfactant can include a $C_6$-$C_{20}$ linear or branched alkylalkoxylated alcohols (AA) having a weight average degree of alkoxylation ranging from 5 to 15, alternatively $C_{12}$-$C_{14}$ linear ethoxylated alcohols having a weight average degree of alkoxylation ranging from 7 to 9. If present, the amount of AA-type nonionic surfactant(s) in the solid sheet OCF article of can range from about 2% to about 40%, alternatively from about 5% to about 30%, alternatively from about 8% to about 12%, by total weight of the solid sheet OCF article.

Amphoteric surfactants suitable for use in the solid sheet OCF article can include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids.

One category of amphoteric surfactants particularly suitable for incorporation into solid sheet OCF articles with personal care applications (e.g., shampoo, facial or body cleanser, and the like) include alkylamphoacetates, such as lauroamphoacetate and cocoamphoacetate. Alkylamphoacetates can be comprised of monoacetates and diacetates. In some types of alkylamphoacetates, diacetates are impurities or unintended reaction products. If present, the amount of alkylamphoacetate(s) in the solid sheet OCF article may range from about 2% to about 40%, alternatively from about 5% to about 30%, alternatively from about 10% to about 20%, by total weight of the solid sheet OCF article.

Zwitterionic surfactants suitable include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

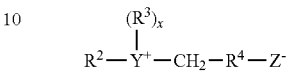

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical, wherein R is a $C_{11}$-$C_{17}$ alkyl, is attached to the nitrogen atom of the betaine are also useful in this invention.

Cationic surfactants can also be utilized in the OCF articles, especially in fabric softener and hair conditioner products. When used in making products that contain cationic surfactants as the major surfactants, such cationic surfactants can be present in an amount ranging from about 2% to about 30%, alternatively from about 3% to about 20%, alternatively from about 5% to about 15% by total weight of the solid sheet OCF article.

Cationic surfactants may include DEQA compounds, which encompass a description of diamido actives as well as actives with mixed amido and ester linkages. DEQA compounds are typically made by reacting alkanolamines such as MDEA (methyldiethanolamine) and TEA (triethanolamine) with fatty acids. Some materials that typically result from such reactions include N,N-di(acyl-oxyethyl)-N, N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids.

Other suitable actives for use as a cationic surfactant include reaction products of fatty acids with dialkylenetriamines in, e.g., a molecular ratio of about 2:1, said reaction products containing compounds of the formula:

wherein $R^1$, $R^2$ are defined as above, and each $R^3$ is a $C_{1-6}$ alkylene group, alternatively an ethylene group. Examples of these actives are reaction products of tallow acid, canola acid, or oleic acids with diethylenetriamine in a molecular ratio of about 2:1, said reaction product mixture containing N,N''-ditallowoyldiethylenetriamine, N,N''-dicanola-oyldiethylenetriamine, or N,N''-dioleoyldiethylenetriamine, respectively, with the formula:

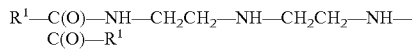
$$R^1-C(O)-NH-CH_2CH_2-NH-CH_2CH_2-NH-C(O)-R^1$$

wherein $R^2$ and $R^3$ are divalent ethylene groups, $R^1$ is defined above and an acceptable examples of this structure when $R^1$ is the oleoyl group of a commercially available oleic acid derived from a vegetable or animal source, include EMERSOL® 223LL or EMERSOL® 7021, available from Henkel Corporation.

Another active for use as a cationic surfactant has the formula:

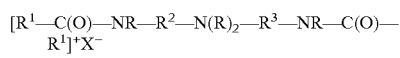
$$[R^1-C(O)-NR-R^2-N(R)_2-R^3-NR-C(O)-R^1]^+X^-$$

wherein R, $R^1$, $R^2$, $R^3$ and $X^-$ are defined as above. Examples of this active are the di-fatty amidoamines based softener having the formula:

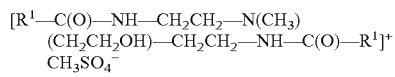
$$[R^1-C(O)-NH-CH_2CH_2-N(CH_3)(CH_2CH_2OH)-CH_2CH_2-NH-C(O)-R^1]^+$$
$$CH_3SO_4^-$$

wherein $R^1$—C(O) is an oleoyl group, soft tallow group, or a hardened tallow group available commercially from Degussa under the trade names VARISOFT® 222LT, VARISOFT® 222, and VARISOFT® 110, respectively.

A second type of DEQA ("DEQA (2)") compound suitable as a active for use as a cationic surfactant has the general formula:

$$[R_3N^+CH_2CH(YR^1)(CH_2YR^1)]^+X^-$$

wherein each Y, R, $R^1$, and $X^-$ have the same meanings as before. The DEQA (2) can be the "propyl" ester quaternary ammonium fabric softener active having the formula 1,2-di (acyloxy) trimethylammoniopropane chloride.

Suitable polymeric surfactants for use in the personal care compositions can include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

Plasticizers

The OCF article can optionally comprises a plasticizer, in the amount ranging from about 0.1% to about 25%, alternatively from about 0.5% to about 20%, alternatively from about 1% to about 15%, most alternatively from 2% to 12%, by total weight of said solid sheet OCF article. Correspondingly, the wet pre-mixture used for forming such solid sheet OCF article may comprise from about 0.02% to about 20% by weight of said wet pre-mixture, in one embodiment from about 0.1% to about 10% by weight of said wet pre-mixture, in one embodiment from about 0.5% to about 5% by weight of the wet pre-mixture.

Suitable plasticizers can include, for example, polyols, copolyols, polycarboxylic acids, polyesters, dimethicone copolyols, and the like.

Polyols can include, but are not limited to: glycerin, diglycerin, ethylene glycol, polyethylene glycol (especially 200-600), propylene glycol, butylene glycol, pentylene glycol, glycerol derivatives (such as propoxylated glycerol), glycidol, cyclohexane dimethanol, hexanediol, 2,2,4-trimethylpentane-1,3-diol, pentaerythritol, urea, sugar alcohols (such as sorbitol, mannitol, lactitol, xylitol, maltitol, and other mono- and polyhydric alcohols), mono-, di- and oligosaccharides (such as fructose, glucose, sucrose, maltose, lactose, high fructose corn syrup solids, and dextrins), ascorbic acid, sorbates, ethylene bisformamide, amino acids, and the like.

Polycarboxylic acids can include, but are not limited to citric acid, maleic acid, succinic acid, polyacrylic acid, and polymaleic acid.

Polyesters can include, but are not limited to, glycerol triacetate, acetylated-monoglyceride, diethyl phthalate, triethyl citrate, tributyl citrate, acetyl triethyl citrate, acetyl tributyl citrate.

Suitable dimethicone copolyols can include, but are not limited to, PEG-12 dimethicone, PEG/PPG-18/18 dimethicone, and PPG-12 dimethicone.

Other suitable platicizers can include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

In one example, the plasticizers can include glycerin, ethylene glycol, polyethylene glycol, propylene glycol, and mixtures thereof. In one example, the plasticizer can comprise glycerin.

Additional Ingredients

In addition to the above-described ingredients, e.g., the water-soluble polymer, the surfactant(s) and the plasticizer, the OCF article may comprise one or more additional ingredients, depending on its intended application. Such one or more additional ingredients may be selected from the group consisting of fabric care actives, dishwashing actives, hard surface cleaning actives, beauty and/or skin care actives, personal cleansing actives, hair care actives, oral care actives, feminine care actives, baby care actives, and any combinations thereof.

Suitable fabric care actives can include but are not limited to: organic solvents (linear or branched lower $C_1$-$C_8$ alcohols, diols, glycerols or glycols; lower amine solvents such as $C_1$-$C_4$ alkanolamines, and mixtures thereof; more specifically 1,2-propanediol, ethanol, glycerol, monoethanolamine and triethanolamine), carriers, hydrotropes, builders, chelants, dispersants, enzymes and enzyme stabilizers, catalytic materials, bleaches (including photobleaches) and bleach activators, perfumes (including encapsulated perfumes or perfume microcapsules), colorants (such as pigments and dyes, including hueing dyes), brighteners, dye transfer inhibiting agents, clay soil removal/anti-redeposition agents, structurants, rheology modifiers, suds suppressors, processing aids, fabric softeners, anti-microbial agents, and the like.

Suitable hair care actives can include but are not limited to: moisture control materials of class II for frizz reduction (salicylic acids and derivatives, organic alcohols, and esters), cationic surfactants (especially the water-insoluble type having a solubility in water at 25° C. below 0.5 g/100 g of water, alternatively below 0.3 g/100 g of water), high melting point fatty compounds (e.g., fatty alcohols, fatty acids, and mixtures thereof with a melting point of 25° C. or higher, alternatively 40° C. or higher, alternatively 45° C. or higher, alternatively 50° C. or higher), silicone compounds, conditioning agents (such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients), preservatives (such as benzyl alcohol, methyl paraben, propyl paraben and imidazolidinyl urea), pH adjusting agents (such as citric acid, sodium citrate, succinic acid, phosphoric acid, sodium hydroxide, sodium carbonate), salts (such as potassium acetate and sodium chloride), coloring agents, perfumes or fragrances, sequestering agents (such as disodium ethylenediamine tetra-acetate), ultraviolet and infrared screening and absorbing agents (such as octyl salicylate), hair bleaching agents, hair perming agents, hair fixatives, anti-dandruff agents, anti-microbial agents, hair growth or restorer agents, co-solvents or other additional solvents, and the like.

Suitable beauty and/or skin care actives can include those materials approved for use in cosmetics and that are described in reference books such as the CTFA Cosmetic Ingredient Handbook, Second Edition, The Cosmetic, Toiletries, and Fragrance Association, Inc. 1988, 1992. Further non-limiting examples of suitable beauty and/or skin care actives include preservatives, perfumes or fragrances, coloring agents or dyes, thickeners, moisturizers, emollients, pharmaceutical actives, vitamins or nutrients, sunscreens, deodorants, sensates, plant extracts, nutrients, astringents, cosmetic particles, absorbent particles, fibers, anti-inflammatory agents, skin lightening agents, skin tone agent (which functions to improve the overall skin tone, and may include vitamin B3 compounds, sugar amines, hexamidine compounds, salicylic acid, 1,3-dihydroxy-4-alkybenzene such as hexylresorcinol and retinoids), skin tanning agents, exfoliating agents, humectants, enzymes, antioxidants, free radical scavengers, anti-wrinkle actives, anti-acne agents, acids, bases, minerals, suspending agents, pH modifiers, pigment particles, anti-microbial agents, insect repellents, shaving lotion agents, co-solvents or other additional solvents, and the like.

The solid sheet OCF article may further comprise other optional ingredients that are known for use or otherwise useful in compositions, provided that such optional materials are compatible with the selected essential materials described herein, or do not otherwise unduly impair product performance.

Non-limiting examples of product type embodiments that can be formed by the solid sheet OCF article of the present invention can include laundry detergent products, fabric softening products, hand cleansing products, hair shampoo products, hair conditioning products, hair styling products including hair treatment products, body cleansing products, shaving preparation products, dish cleaning products, personal care substrates containing pharmaceutical or other skin care actives, moisturizing products, sunscreen products, beauty or skin care products, deodorizing products, oral care products, feminine cleansing products, baby care products, fragrance-containing products, and so forth.

Process for Making Open Cell Foam Articles

WO2010077627 and WO2012138820, incorporated by reference, disclose processes for forming flexible, porous, dissolvable solid sheet OCF articles with OCF structures by first preparing a pre-mixture containing various materials, then aerating the pre-mixture by introducing a gas thereinto, followed by forming the aerated pre-mixture into a sheet, and finally drying the sheet at an elevated temperature. The OCF structures are formed during the drying step under simultaneous mechanisms of water evaporation, bubble collapse, interstitial liquid drainage from the thin film bubble facings into the plateau borders between the bubbles (which generates openings between the bubbles and forms the open cells), and solidification of the pre-mixture. Various processing conditions may influence these mechanisms, e.g., solid content in the wet pre-mixture, viscosity of the wet pre-mixture, gravity, and the drying temperature, and the need to balance such processing conditions so as to achieve controlled drainage and form the desired OCF structures.

The OCF articles described, including the article in Table 3, can be made with the following steps of: (a) forming a pre-mixture containing raw materials (e.g., the water-soluble polymer, active ingredients such as surfactants, and optionally a plasticizer) dissolved or dispersed in water or a suitable solvent, which is characterized by a viscosity of from about 1,000 cps to about 25,000 cps measured at about 40° C. and 1 $s^{-1}$; (b) aerating said pre-mixture (e.g., by introducing a gas into the wet slurry) to form an aerated wet pre-mixture; (c) forming said aerated wet pre-mixture into a sheet having opposing first and second sides; and (d) drying said formed sheet for a drying time of from 1 minute to 60 minutes at a temperature from 70° C. to 200° C. along a heating direction that forms a temperature gradient decreasing from the first side to the second side of said formed sheet, wherein the heating direction is substantially offset from the gravitational direction for more than half of the drying time, i.e., the drying step is conducted under heating along a mostly "anti-gravity" heating direction. Such a mostly "anti-gravity" heating direction can be achieved by various means, which include but are not limited to the bottom conduction-based heating/drying arrangement and the rotary drum-based heating/drying arrangement, as illustrated hereinabove in FIGS. 4 and 5 respectively.

When making the OCF articles it can be desirable to carefully adjust the viscosity and/or solid content of the wet pre-mixture, the amount and speed of aeration (air feed pump speed, mixing head speed, air flow rate, density of the aerated pre-mixture and the like, which may affect bubble sizes and quantities in the aerated pre-mixture and correspondingly impact the pore size/distribution/quantity/characteristics in the solidified sheet article), the drying temperature and the drying time, in order to achieve optimal OCF structure in the resulting sheet article. In addition, it can be important to have the desired heating direction (i.e., in a substantially offset relation with respect to the gravitational direction).

Step (A): Preparation of Wet Pre-Mixture

The wet pre-mixture can be prepared by mixing solids of interest, including the water-soluble polymer, surfactant(s) and/or other benefit agents, optional plasticizer, and other optional ingredients, with a sufficient amount of water or another solvent in a pre-mix tank. The wet pre-mixture can be formed using a mechanical mixer. Mechanical mixers useful herein, include, but aren't limited to pitched blade turbines or MAXBLEND mixer (Sumitomo Heavy Industries).

It The viscosity of the wet pre-mixture can be adjusted to be from about 1,000 cps to about 25,000 cps when measured at 40° C. and 1 $s^{-1}$. Viscosity of the wet pre-mixture can impact the pore expansion and pore opening of the aerated pre-mixture during the subsequent drying step. The viscosity of the wet pre-mixture can range from about 3,000 cps to about 24,000 cps, alternatively from about 5,000 cps to about 23,000 cps, and alternatively from about 10,000 cps to about 20,000 cps, as measured at 40° C. and 1 sec$^{-1}$. The pre-mixture viscosity values are measured using a Malvern Kinexus Lab+ rheometer with cone and plate geometry (CP1/50 SR3468 SS), a gap width of 0.054 mm, a temperature of 40° C. and a shear rate of 1.0 reciprocal seconds for a period of 360 seconds.

The wet pre-mixture can contain at from about 15% to about 70% solids, alternatively from about 20% to about 50%, and alternatively from about 25% to about 45% by total weight of said wet pre-mixture. The percent solid content is the summation of the weight percentages by weight of the total processing mixture of all solid components, semi-solid components and liquid components excluding water and any obviously volatile materials such as low boiling alcohols.

Among the solids of interest in the wet pre-mixture can contain from about 1% to about 75% surfactant(s), from about 0.1% to about 25% water-soluble polymer, and optionally from about 0.1% to about 25% plasticizer, by total weight of the solids. Other actives or benefit agents can also be added into the pre-mixture.

Optionally, the wet pre-mixture can pre-heated immediately prior to and/or during the aeration process at above ambient temperature but below any temperatures that would cause degradation of the components therein. The wet pre-mixture can be kept at an elevated temperature ranging from about 40° C. to about 100° C., alternatively from about 50° C. to about 95° C., alternatively from about 60° C. to about 90° C., and alternatively from about 75° C. to about 85° C. Further, additional heat can be applied during the aeration process to try and maintain the wet pre-mixture at such an elevated temperature. This can be accomplished via conductive heating from one or more surfaces, injection of steam or other processing means.

Step (B): Aeration of Wet Pre-Mixture

Aeration of the wet pre-mixture can introduce a sufficient amount of air bubbles into the wet pre-mixture for subsequent formation of the OCF articles therein upon drying. Once sufficiently aerated, the wet pre-mixture is characterized by a density that is significantly lower than that of the non-aerated wet pre-mixture (which may contain a few inadvertently trapped air bubbles) or an insufficiently aerated wet pre-mixture (which may contain some bubbles but at a much lower volume percentage and of significantly larger bubble sizes). The aerated wet pre-mixture can have a density ranging from about 0.05 g/ml to about 0.5 g/ml, alternative from about 0.08 g/ml to about 0.4 g/ml, alternatively from about 0.1 g/ml to about 0.35 g/ml, alternatively from about 0.15 g/ml to about 0.3 g/ml, alternatively from about 0.2 g/ml to about 0.25 g/ml.

Aeration can be accomplished by either physical or chemical means. It can be accomplished by introducing a gas into the wet pre-mixture through mechanical agitation, for example, by using any suitable mechanical processing means, including but not limited to: a rotor stator mixer, a planetary mixer, a pressurized mixer, a non-pressurized mixer, a batch mixer, a continuous mixer, a semi-continuous mixer, a high shear mixer, a low shear mixer, a submerged sparger, or any combinations thereof. Alternatively, it can be achieved via chemical means, for example, by using chemical foaming agents to provide in-situ gas formation via chemical reaction of one or more ingredients, including formation of carbon dioxide ($CO_2$ gas) by an effervescent system.

Bubble size of the aerated wet pre-mixture can assist in achieving uniform layers in the OCF articles of the resulting solid sheet OCF article. In example, the bubble size of the aerated wet pre-mixture can be from about 5 to about 100 microns, and alternatively from about 20 microns to about 80 microns.

Step (C): Sheet-Forming

After sufficient aeration, the aerated wet pre-mixture forms one or more sheets with opposing first and second sides. The sheet-forming step can be conducted in any suitable manners, e.g., by extrusion, casting, molding, vacuum-forming, pressing, printing, coating, and the like. More specifically, the aerated wet pre-mixture can be formed into a sheet by: (i) casting it into shallow cavities or trays or specially designed sheet molds; (ii) extruding it onto a continuous belt or screen of a dryer; (iii) coating it onto the outer surface of a rotary drum dryer. The supporting surface upon which the sheet is formed can be formed by or coated with materials that are anti-corrosion, non-interacting and/or non-sticking, such as metal (e.g., steel, chromium, and the like), TEFLON®, polycarbonate, NEOPRENE®, HDPE, LDPE, rubber, glass and the like.

The formed sheet of aerated wet pre-mixture can have a thickness from about 0.5 mm to about 4 mm, alternatively from about 0.6 mm to about 3.5 mm, alternatively from about 0.7 mm to about 3 mm, alternatively from about 0.8 mm to about 2 mm, alternatively from about 0.9 mm to about 1.5 mm Controlling the thickness of such formed sheet of aerated wet pre-mixture may be important for ensuring that the resulting solid sheet OCF article has the desired OCF structures. If the formed sheet is too thin (e.g., less than 0.5 mm in thickness), many of the air bubbles trapped in the aerated wet pre-mixture will expand during the subsequent drying step to form through-holes that extend through the entire thickness of the resulting solid sheet OCF article. Such through-holes, if too many, may significantly compromise both the overall structural integrity and aesthetic appearance of the sheet article. If the formed sheet is too thick, not only it will take longer to dry, but also it will result in a solid sheet OCF article with greater pore size variations between different regions (e.g., top, middle, and bottom regions) along its thickness, because the longer the drying time, the more imbalance of forces may occur through bubble rupture/collapse/coalescence, liquid drainage, pore expansion, pore opening, water evaporation, and the like.

Step D: Drying under Anti-Gravity Heating

After the sheet is formed, anti-gravity heating direction during the drying step, either through the entire drying time or at least through more than half of the drying time, can be used.

Figure 4:
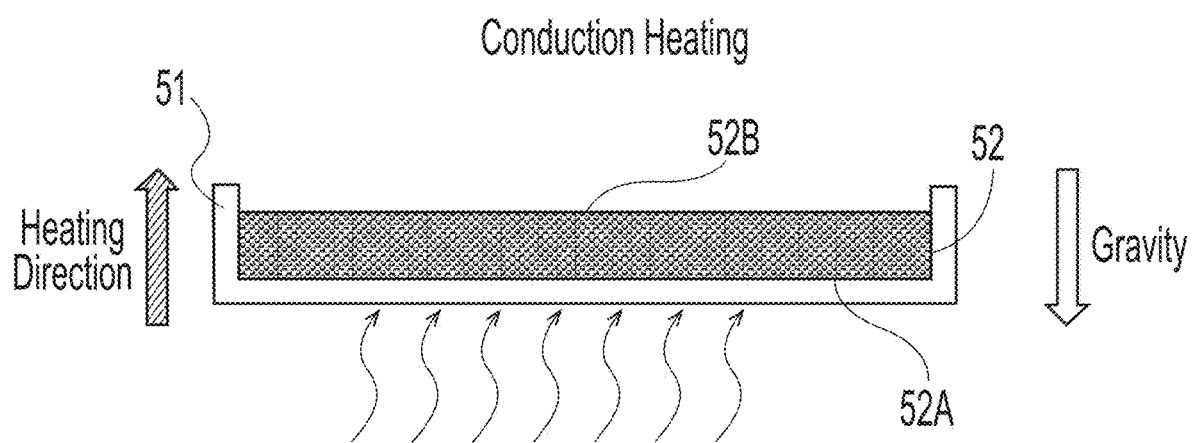
FIG. 4 shows a bottom conduction-based heating/drying arrangement for making a flexible, porous, dissolvable sheet in a batch process.

In a specific embodiment, the anti-gravity heating direction is provided by a conduction-based heating/drying arrangement, either the same or similar to that illustrated by FIG. 4.

FIG. 4 shows a bottom conduction-based heating/drying arrangement for making an inventive flexible, porous, dissolvable OCF sheet. Specifically, a mold 51 is filled with an aerated wet pre-mixture, which forms a sheet 52 having a first side 52A (i.e., the bottom side) and an opposing second side 52B (i.e., the top side). Such mold 51 is placed on a heated surface (not shown), for example, on top of a pre-heated Peltier plate with a controlled surface temperature of about 125-130° C., for approximately 30 minutes during the drying step. Heat is conducted from the heated surface at the bottom of the mold 51 through the mold to heat the sheet 52 from below, i.e., along an upward heating direction (as shown by the cross-hatched arrowhead), which forms a temperature gradient in said sheet 52 that decreases from the first side 52A (the bottom side) to the opposing second side 52B (the top side). Such an upward heating direction is opposite to the gravitational direction (as shown by the white arrowhead), and it is maintained as so throughout the entire drying time (i.e., the heating direction is opposite to the gravitational direction for almost 100% of the drying time). During drying, the gravitational force still drains the liquid pre-mixture downward toward the bottom region. However, the upward heating direction dries the sheet from bottom up, and water vapor generated by heat at the bottom region arises upward to escape from the solidifying matrix, so the downward liquid drainage toward the bottom region is significantly limited and "counteracted"/reduced by the solidifying matrix and the uprising water vapor. Correspondingly, the bottom region of the resulting dry sheet is less dense and contains numerous pores with relatively thin cell walls. Further, because the top region is the last region that is dried during this process, the air bubbles in the top region have sufficient time to expand to form significantly larger open pores at the top surface of the resulting sheet, which are particularly effective in facilitating water ingress into the sheet. Moreover, the resulting sheet article has a more evenly distributed overall pore sizes throughout different regions (e.g., top, middle, bottom) thereof.

Figure 5:
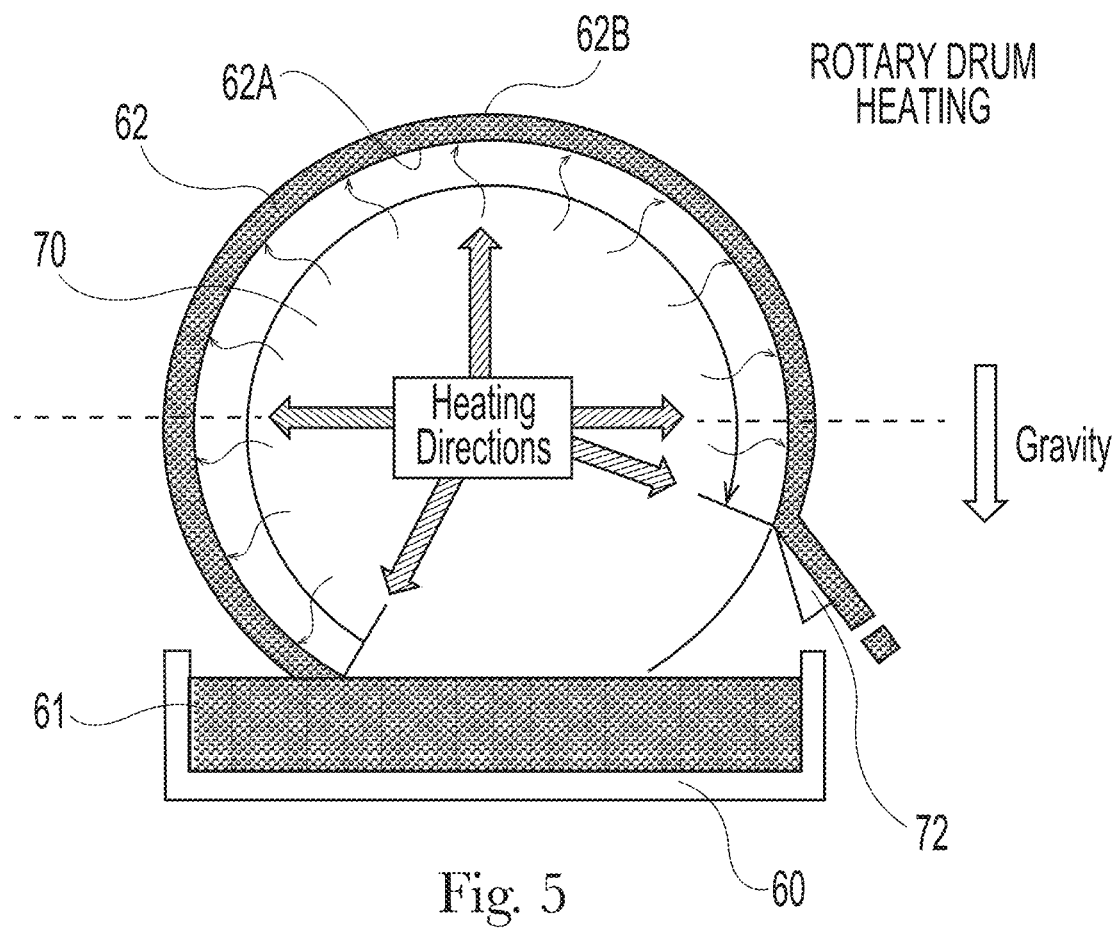
FIG. 5 shows a rotary drum-based heating/drying arrangement for making flexible, porous, dissolvable sheet in a continuous process.

Alternatively, the anti-gravity heating direction is provided by a rotary drum-based heating/drying arrangement, which is also referred to as drum drying or roller drying, similar to that illustrated in FIG. 5.

FIG. 5 shows a rotary drum-based heating/drying arrangement that can also be used to make a flexible, porous, dissolvable OCF sheet. Specifically, a feeding trough 60 is filled with an aerated wet pre-mixture 61. A heated rotatable cylinder 70 (also referred to as a drum dryer) is placed above said feeding trough 60. Said heated drum dryer 70 has a cylindrical heated outer surface characterized by a controlled surface temperature of about 130° C., and it rotates along a clock-wise direction (as shown by the thin curved line with an arrowhead) to pick up the aerated wet pre-mixture 61 from the feeding trough 60. The aerated wet pre-mixture 61 forms a thin sheet 62 over the cylindrical heated outer surface of the drum dryer 70, which rotates and dries such sheet 62 of aerated wet pre-mixture in approximately 10-15 minutes. A leveling blade (not shown) may be placed near the slurry pick-up location to ensure a consistent thickness of the sheet 62 so formed, although it is possible to control the thickness of sheet 62 simply by modulating the viscosity of the aerated wet pre-mixture 61 and the rotating speed and surface temperature of the drum dryer 70. Once dried, the sheet 62 can then picked up, either manually or by a scraper 72 at the end of the drum rotation.

As shown in FIG. 5, the sheet 62 formed by the aerated wet pre-mixture 61 comprises a first side 62A (i.e., the bottom side) that directly contacts the heated outer surface of the heated drum dryer 70 and an opposing second side 62B (i.e., the top side). Correspondingly, heat from the drum dryer 70 is conducted to the sheet 62 along an outward heating direction, to heat the first side 62A (the bottom side) of the sheet 62 first and then the opposing second side 62B (the top side). Such outward heating direction forms a temperature gradient in the sheet 62 that decreases from the first side 62A (the bottom side) to the opposing second side 62B (the top side). The outward heating direction is slowly and constantly changing as the drum dryer 70 rotates, but along a very clear and predictable path (as shown by the multiple outwardly extending cross-hatched arrowheads in FIG. 4). The relative position of the outward heating direction and the gravitational direction (as shown by the white arrowhead) is also slowing and constantly changing in a similar clear and predictable manner. For less than half of the drying time (i.e., when the heating direction is below the horizontal dashed line), the outward heating direction is substantially aligned with the gravitational direction with an offset angle of less than 90° in between. During majority of the drying time (i.e., when the heating direction is flushed with or above the horizontal dashed line), the outward heating direction is opposite or substantially opposite to the gravitational direction with an offset angle of 90° or more therebetween. Depending on the initial "start" coating position of the sheet 62, the heating direction can be opposite or substantially opposite to the gravitational direction for more than 55% of the drying time (if the coating starts at the very bottom of the drum dryer 70), alternatively more than 60% of the drying time (if the coating starts at a higher position of the drum dryer 70, as shown in FIG. 5). Consequently, during most of the drying step this slowing rotating and changing heating direction in the rotary drum-based heating/drying arrangement can still function to limit and "counteract"/reduce the liquid drainage in sheet 62 caused by the gravitational force, resulting in improved OCF structures in the sheet article so formed. The resulting sheet article as dried by the heated drum dryer 70 is also characterized by a less dense bottom region with numerous more evenly sized pores, and a top surface with relatively larger pore openings. Moreover, the resulting sheet article has a more evenly distributed overall pore sizes throughout different regions (e.g., top, middle, bottom) thereof.

Converting Multiple Sheets into Multilayer Structures

Once the flexible, dissolvable, porous solid sheets are formed, as described hereinabove, two or more of such sheets can be further combined and/or treated to form dissolvable solid OCF articles of any desirable three-dimensional shapes, including but not limited to: spherical, cubic, rectangular, oblong, cylindrical, rod, sheet, flower-shaped, fan-shaped, star-shaped, disc-shaped, and the like. The sheets can be combined and/or treated by any means known in the art, examples of which include but are not limited to, chemical means, mechanical means, and combinations thereof. Such combination and/or treatment steps are hereby collectively referred to as a "conversion" process, i.e., which functions to convert two or more flexible, dissolvable, porous OCF sheets into a dissolvable solid article with a desired three-dimensional shape.

The multilayer dissolvable solid OCF articles formed by stacking multiple layers of the solid sheet OCF articles together is characterized by a maximum dimension D and a minimum dimension z (which is perpendicular to the maximum dimension), while the ratio of D/z (hereinafter also referred to as the "Aspect Ratio") ranges from 1 to about 10, alternatively from about 1.4 to about 9, alternatively from about 1.5 to about 8, alternatively from about 2 to about 7. Note that when the Aspect Ratio is 1, the dissolvable solid article has a spherical shape. When the Aspect Ratio is about 1.4, the dissolvable solid article has a cubical shape.

The multilayer dissolvable solid OCF article may have a minimal dimension z that is greater than about 3 mm but less than about 20 cm, alternatively from about 4 mm to about 10 cm, alternatively from about 5 mm to about 30 mm.

The above-described multilayer dissolvable solid OCF article may comprise more than two of such flexible, dissolvable, porous sheets. For example, it may comprise from about 4 to about 50, alternatively from about 5 to about 40, alternatively from about 6 to about 30, of said flexible, dissolvable, porous sheets. The improved OCF structures in the flexible, dissolvable, porous sheets allow stacking of many sheets (e.g., 15-40) together, while still providing a satisfactory overall dissolution rate for the stack.

In one example, the multilayer dissolvable solid article can comprise from 15 to 40 layers of the above-described flexible, dissolvable, porous sheets and has an aspect ratio ranging from about 2 to about 7.

Table 4 to Table 11, hereafter, show examples of various solid OCF articles intended for laundry care and hair care.

Wet pre-mixtures with the following surfactant/polymer compositions as described in Table 4 and Table 5 below are prepared, for laundry care and hair care articles, respectively.

TABLE 4

Laundry Care Formulation

|  | (Wet) w/w % | (Dry) w/w % |
|---|---|---|
| Polyvinyl alcohol (with a degree of polymerization of about 1700) | 7.58 | 21 |
| Glycerin | 1.08 | 3 |
| Linear Alkylbenzene Sulfonate | 19.12 | 53 |
| Sodium Laureth-3 Sulfate | 3.61 | 10 |
| C12-C14 Ethoxylated alcohol | 3.61 | 10 |
| Water | Balance | Balance |

Viscosity of the wet pre-mixture composition as described in Table 4 is about 14309.8 cps. After aeration, the average density of such aerated wet pre-mixture is about 0.25 g/cm$^3$.

TABLE 5

Hair Care Formulation - Shampoo

| Materials: | (Wet) w/w % | (Dry) w/w % |
|---|---|---|
| Polyvinyl alcohol (with a degree of polymerization of about 1700) | 6.85 | 23.69 |
| Glycerin | 2.75 | 9.51 |
| Sodium Lauryl Sulfate | 9.52 | 32.89 |
| Sodium Laureth-3 Sulfate | 3.01 | 10.42 |
| Sodium Lauroamphoacetate | 5 | 17.28 |
| Citric acid (anhydrous) | 0.93 | 3.21 |
| Water | Balance | Balance |

Viscosity of the wet pre-mixture composition as described in Table 5 is about 19254.6 cps. After aeration, the average density of such aerated wet pre-mixture is about 0.225 g/cm$^3$.

Flexible, porous, dissolvable solid sheet OCF articles A and B are prepared from the above wet pre-mixtures as described in Table 4 and Table 5 using a continuous aerator (Aeros) and a rotary drum drier, with the following settings and conditions as described in Table 6 below:

TABLE 6

Drum Drying

| Parameters | Value |
|---|---|
| Wet pre-mixture temperature before and during aeration | 80° C. |
| Aeros feed pump speed setting | 600 |

TABLE 6-continued

Drum Drying

| Parameters | Value |
|---|---|
| Aeros mixing head speed setting | 500 |
| Aeros air flow rate setting | 100 |
| Wet pre-mixture temperature before drying | 60° C. |
| Rotary drum drier surface temperature | 130° C. |
| Rotary drum drier rotational speed | 0.160 rpm |
| Drying time | 4.52 min |

A flexible, porous, dissolvable solid sheet OCF article C is also prepared from the above wet pre-mixture as described in Table 4 using a continuous aerator (Oakes) and a mold placed on a hot plate (which provides bottom conduction-based heating), with the following settings and conditions as described in Table 7 below:

TABLE 7

Hot Plate Drying

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Hot plate surface temperature | 130° C. |
| Drying time | 12.5 min |

Further, flexible, porous, dissolvable solid sheet OCF articles are prepared from the above wet pre-mixtures described in Table 4 and Table 5 using a continuous aerator (Oakes) and a mold placed on an impingement oven, with the following settings and conditions as described in Table 8 below:

TABLE 8

Impingement Oven Drying

| Parameters | Value |
|---|---|
| Wet pre-mixture temperature before and during aeration | 80° C. |
| Oakes air flow meter setting | 19.2 L/hour |
| Oakes pump meter speed setting | 20 rpm |
| Oakes mixing head speed | 1500 rpm |
| Mold depth | 1.0 mm |
| Impingement oven temperature | 130° C. |
| Drying time | 6 min |

Table 9 to Table 11 as follows summarize various physical parameters and pore structures measured for the inventive solid sheet OCF articles A-C and I-II made from the above-described wet pre-mixtures and drying processes.

TABLE 9

Physical Parameters

| Samples | Formulation | Drying Process | Average Basis Weight gsm | Average Density g/cm³ | Average Thickness mm | Specific Surface Area m²/g |
|---|---|---|---|---|---|---|
| A | Laundry Care (Table 4) | Rotary Drum | 147.5 | 0.118 | 1.265 | 0.115 |
| B | Hair Care (Table 5) | Rotary Drum | 138.4 | 0.111 | 1.254 | 0.107 |
| C | Hair Care (Table 5) | Hot Plate | 216.3 | 0.111 | 1.968 | — |
| I | Laundry Care (Table 4) | Impingement Oven | 116.83 | 0.118 | 1.002 | — |
| II | Hair Care (Table 5) | Impingement Oven | 212.9 | 0.111 | 1.929 | — |

TABLE 10

Overall Pore Structures

| Samples | Formulation | Drying Process | Percent Open Cell Content % | Overall Average Pore Size μm | Average Cell Wall Thickness μm |
|---|---|---|---|---|---|
| A | Laundry Care (Table 4) | Rotary Drum | 90.75 | 467.1 | 54.3 |
| B | Hair Care (Table 5) | Rotary Drum | 93.54 | 466.9 | 42.8 |
| C | Hair Care (Table 5) | Hot Plate | — | 287.4 | 19.7 |
| I | Laundry Care (Table 4) | Impingement Oven | — | 197.6 | 15.2 |
| II | Hair Care (Table 5) | Impingement Oven | — | 325.1 | 18.7 |

TABLE 11

Surface and Regional Pore Structures

| Samples | Formulation | Drying Process | Surface Average Pore Diameter (μm) Top | Average Pore Size (μm) Top | Middle | Bottom |
|---|---|---|---|---|---|---|
| A | Laundry Care (Table 4) | Rotary Drum | 201.5 | 458.3 | 479.1 | 463.9 |
| B | Hair Care (Table 5) | Rotary Drum | 138.2 | 412.4 | 519.0 | 469.1 |
| C | Hair Care (Table 5) | Hot Plate | 120.8 | 259.7 | 292.0 | 309.9 |
| I | Laundry Care (Table 4) | Impingement Oven | 53.3 | 139.9 | 213.1 | 238.7 |
| II | Hair Care (Table 5) | Impingement Oven | 60.0 | 190.7 | 362.6 | 419.6 |

Table 12 to Table 17, hereafter, show examples of various solid OCF articles intended for personal care, laundry care, and fabric enhancers.

TABLE 12

Personal Care Formulation

| Chemical | (Wet) w/w % | (Dry) w/w % |
|---|---|---|
| Polyvinyl alcohol (Degree of polymerization 1700) | 8.1 | 23.5 |
| Glycerin | 3.2 | 9.4 |
| Sodium Laureth-3 Sulfate | 1.5 | 4.4 |
| Sodium Laureth-1 Sulfate | 13.3 | 38.5 |
| Sodium Lauroamphoacetate | 5.9 | 17.1 |
| Guar Hydroxypropyltrimonium Chloride | 0.4 | 1.2 |
| Citric acid (anhydrous) | 1.0 | 2.9 |
| Water | Balance | Balance |

TABLE 13

Personal Care Formulation

| Chemical | (Wet) w/w % | (Dry) w/w % |
|---|---|---|
| Polyvinyl alcohol (Degree of polymerization 1700) | 8.5 | 24.5 |
| Glycerin | 3.2 | 9.3 |
| Sodium Lauryl Sulfate (unethoxylated) | 13.1 | 37.7 |
| Sodium Laureth-3 Sulfate | 3.6 | 10.2 |
| Sodium Lauroamphoacetate | 4.0 | 11.5 |
| Guar Hydroxypropyltrimonium Chloride | 0.4 | 1.2 |

TABLE 13-continued

Personal Care Formulation

| Chemical | (Wet) w/w % | (Dry) w/w % |
|---|---|---|
| Citric acid (anhydrous) | 0.7 | 2.1 |
| Sodium Benzoate | 0.2 | 0.5 |
| Water | Balance | Balance |

TABLE 14

Laundry Care Formulation

| Chemical | (Wet) w/w % | (Dry) w/w % |
|---|---|---|
| Polyvinyl alcohol (Degree of polymerization 1700) | 7.6 | 21.0 |
| Glycerin | 1.1 | 3.0 |
| Linear Alkylbenzene Sulfonate | 19.1 | 52.9 |
| Sodium Laureth-3 Sulfate | 3.6 | 10.0 |
| C12-C14 Ethoxylated alcohol | 3.6 | 10.0 |
| Water | Balance | Balance |

TABLE 15

Laundry Care Formulation

| Chemical | (Wet) w/w % | (Dry) w/w % |
|---|---|---|
| Polyvinyl alcohol (Degree of polymerization 1700) | 3.1 | 6.9 |
| Polyvinyl alcohol (Degree of polymerization 500) | 6.2 | 13.9 |
| Glycerin | 3.1 | 6.9 |
| Sodium Lauryl Sulfate (Unethoxylated) | 17.4 | 39.3 |
| Sodium C14-C16 alpha olefin sulfonate | 13.3 | 30.0 |
| Water | Balance | Balance |

TABLE 16

Fabric Enhancer Formula

| Chemical | (Wet) w/w % | (Dry) w/w % |
|---|---|---|
| Polyvinyl alcohol (Degree of polymerization 1700) | 7.2 | 20.0 |
| Glycerin | 7.2 | 20.0 |
| C12-C14 Ethoxylated alcohol | 9.1 | 25.1 |
| Citric acid (anhydrous) | 1.5 | 4.1 |
| Ethanaminium, 2-hydroxy-N-(2-hydroxyethyl)-N,N-dimethyl-, esters with C16-18 and C18-unsatd. fatty acids, chlorides | 9.0 | 25.0 |
| 2-Propanol | 1.0 | 2.8 |
| Water | Balance | Balance |

Flexible, porous, dissolvable solid sheets with OCF structures are prepared from the above wet pre-mixtures 1-5 as described in Table 12 to Table 16 using a continuous aerator (Aeros) and a rotary drum drier, with the following settings and conditions as described in Table 17 below:

TABLE 17

Drum Drying

| Parameters | Value |
|---|---|
| Wet pre-mixture temperature before and during aeration | 80° C. |
| Aeros feed pump speed setting | 600 |
| Aeros mixing head speed setting | 500 |
| Aeros air flow rate setting | 100 |

TABLE 17-continued

Drum Drying

| Parameters | Value |
|---|---|
| Wet pre-mixture temperature before drying | 60° C. |
| Rotary drum drier surface temperature | 130° C. |
| Rotary drum drier rotational speed | 0.118 rpm |
| Drying time | 6.81 min |

Test Methods

Test 1: Hand Dissolution Test Method

Materials Needed:

Articles to be tested: 3-5 samples are tested so that an average of the number of strokes for each if the individual sample is calculated and recorded as the Average Hand Dissolution value. For this method, the entire consumer saleable or consumer sample is tested. If the entire consumer saleable or consumer use sample is a pad with a footprint greater than 50 cm$^2$, then first cut the article to have a footprint of 50 cm$^2$.

Nitrile Gloves 10 cc syringe

Plastic Weigh boat (~3 in×3 in)

100 mL Glass beaker

Water (City of Cincinnati Water or equivalent having the following properties: Total Hardness=155 mg/L as $CaCO_2$; Calcium content=33.2 mg/L; Magnesium content=17.5 mg/L; Phosphate content=0.0462 mg/L). Water used is water 7 grains per gallon (gpg) hardness and 40° C.+/−5° C.

Protocol:

Add 80 mL of water to glass beaker.

Heat water in beaker until water is at a temperature of 40° C.+/−5° C.

Transfer 15 mL of the water from the beaker into the weigh boat via the syringe.

Within 10 seconds of transferring the water to the weigh boat, place the sample in palm of gloved hand (hand in cupped position in non-dominant hand to hold the sample).

Using dominant hand, add water quickly from the weigh boat to the sample and allow to immediately wet for a period of 5-10 seconds.

Rub with opposite dominant hand (also gloved) in 2 rapid circular strokes.

Visually examine the sample in hand after the 2 strokes. If the sample is completely dissolved, record number of strokes=2 Dissolution Strokes. If not completely dissolved, rub remaining sample for another stroke (3 total) and observe degree of dissolution. If the sample contains no solid pieces after the additional stroke, record number of strokes=3 Dissolution Strokes. If after the 3 strokes total, the sample still contains solid pieces of undissolved sample, continue rubbing in additional circular stroke and check if there are any remaining solid pieces after each additional stroke until the sample is completely dissolved or until reaching a total of 30 strokes, whichever comes first. Record the total number of strokes. Record 30 Dissolution Strokes even if sample pieces remain after the maximum of 30 strokes.

Repeat this process for each of the additional 4 samples. Calculate the arithmetic mean of the recorded values of Dissolution Strokes for the 3-5 samples and record as the Average Hand Dissolution Value for the article. The Average Hand Dissolution Value is reported to the nearest single Dissolution Stroke unit.

Test 2: Stability Test Method

Sachet products (a sealed sachet containing an article or a sealed sachet containing a liquid) are determined to have acceptable Stability Test Method if they have at least a seal strength 75 N/m strength (minimum requirements: easy peel seal), show seal integrity all around the perimeter and satisfy the requirements of the Accelerated Stability Test, as described hereafter.

Test 3: Average Seal Strength

This test method is performed according to ASTM F88. Prepare sealed test specimens for testing by cutting a 1-inch strip of the seal. Edges shall be clean-cut and perpendicular to the direction of seal. Samples were conditioned 36 hours at 72° F.; 50% RH. Each leg of the test specimen was clamped in a peel tester with a pressure of 2.95 bar±0.1. The seal is tested at a rate of grip separation of 300 mm/min. For each cycle, report the maximum force as the specimen is stressed to failure and identify the type of failure. Five specimen per leg are tested to calculate the average seal strength. The average seal strength is defined as: no/weak seal if <75 N/m; easy peel if 75-250 N/m; hard peel if 250-500 N/m; lock seal if more than 500 N/m. Peel seals typically fail adhesively; while lock seals cohesively.

Test 4: Accelerated Stability Test

Sachet products satisfy the Accelerated Stability Test if they have acceptable package integrity, dry article integrity, and article performance, as described below.

Sachet products are tested under accelerated stability conditions (40° C., 75% RH) for a period (e.g. 2 weeks, 4 weeks, 8 weeks, 12 weeks, and/or six months). After the period, five sachet products are visually detected for package integrity. The sachet product has acceptable package integrity if (1) there are no signs of disintegration or delamination of the sachet and the sachet seal is intact, as determined by visual detection and (2) the inner layers of the sachet are inspected for signs of contamination (by visual detection and under 10× microscopy), after the compressive load is applied, as described below.

Then, the sachet product is subjected to an 18 psig (124.1 kPa) compressive load for 15 seconds. and the article is removed from the sachet and stored at 25° C., 60% RH for 1 day. The article is inspected for dry article integrity and article performance. The article has acceptable dry article integrity if by visual detection the article is an integral structure. For example, the article is not considered an integral structure if it fractures or delaminates during the Accelerated Stability Test. The article has acceptable performance if it requires less than 15 strokes in the Hand Dissolution Test, as described herein, and upon visual detection during the hand dissolution test the dissolution is smooth (without chunks or grit) and substantially uniform color.

Test 5: Scanning Electron Microscopic (SEM) Method for Determining Surface Average Pore Diameter of the Sheet Article An Hitachi TM3000 Tabletop Microscope (S/N: 123104-04) is used to acquire SEM micrographs of samples. Samples of the solid sheet OCF articles are approximately 1 cm×1 cm in area and cut from larger sheets. Images are collected at a magnification of 50×, and the unit is operated at 15 kV. A minimum of 5 micrograph images are collected from randomly chosen locations across each sample, resulting in a total analyzed area of approximately 43.0 mm$^2$ across which the average pore diameter is estimated.

The SEM micrographs are then firstly processed using the image analysis toolbox in Matlab. Where required, the images are converted to grayscale. For a given image, a histogram of the intensity values of every single pixel is generated using the 'imhist' Matlab function. Typically, from such a histogram, two separate distributions are obvious, corresponding to pixels of the brighter sheet surface and pixels of the darker regions within the pores. A threshold value is chosen, corresponding to an intensity value between the peak value of these two distributions. All pixels having an intensity value lower than this threshold value are then set to an intensity value of 0, while pixels having an intensity value higher are set to 1, thus producing a binary black and white image. The binary image is then analyzed using ImageJ (https://imagej.nih.gov, version 1.52a), to examine both the pore area fraction and pore size distribution. The scale bar of each image is used to provide a pixel/mm scaling factor. For the analysis, the automatic thresholding and the analyze particles functions are used to isolate each pore. Output from the analyze function includes the area fraction for the overall image and the pore area and pore perimeter for each individual pore detected.

Average Pore Diameter is defined as $D_A 50$:50% of the total pore area is comprised of pores having equal or smaller hydraulic diameters than the $D_A 50$ average diameter.

$$\text{Hydraulic diameter} = \text{'}4*\text{Pore area (m}^2\text{)/Pore perimeter (m)'}.$$

It is an equivalent diameter calculated to account for the pores not all being circular.

Test 6: Micro-Computed Tomographic (μCT) Method for Determining Overall or Regional Average Pore Size and Average Cell Wall Thickness of the Open Cell Foams (OCF)

Porosity is the ratio between void-space to the total space occupied by the OCF. Porosity can be calculated from μCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a μCT X-ray scanning instrument capable of acquiring a dataset at high isotropic spatial resolution. One example of suitable instrumentation is the SCANCO system model 50 μCT scanner (Scanco Medical AG, Brüttisellen, Switzerland) operated with the following settings: energy level of 45 kVp at 133 μA; 3000 projections; 15 mm field of view; 750 ms integration time; an averaging of 5; and a voxel size of 3 μm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from Thermo Fisher Scientific and MATLAB (R2017a) from Mathworks.

Test 7: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet OCF article is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

Open cell percentage=Open cell volume of sample/ Geometric volume of sample*100

It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in "Analytical Methods in Fine particle Technology" by Clyde Orr and Paul Webb.

Test 8: Final Moisture Content of the Sheet Article

Final moisture content of the solid sheet OCF article is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

Test 9: Thickness of the Sheet Article

Thickness of the flexible, porous, dissolvable solid sheet OCF article is obtained by using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1-inch diameter platen weighing about 32 grams, which measures thickness at an application pressure of about 0.09 psi (6.32 gm/cm$^2$).

The thickness of the flexible, porous, dissolvable solid sheet OCF article is measured by raising the platen, placing a section of the sheet article on the stand beneath the platen, carefully lowering the platen to contact the sheet article, releasing the platen, and measuring the thickness of the sheet article in millimeters on the digital readout. The sheet article should be fully extended to all edges of the platen to make sure thickness is measured at the lowest possible surface pressure, except for the case of more rigid substrates which are not flat.

Test 10: Basis Weight of the Sheet Article

Basis Weight of the flexible, porous, dissolvable solid sheet OCF article is calculated as the weight of the sheet article per area thereof (grams/m$^2$). The area is calculated as the projected area onto a flat surface perpendicular to the outer edges of the sheet article. The solid sheet OCF articles are cut into sample squares of 10 cm×10 cm, so the area is known. Each of such sample squares is then weighed, and the resulting weight is then divided by the known area of 100 cm$^2$ to determine the corresponding basis weight.

For an article of an irregular shape, if it is a flat object, the area is thus computed based on the area enclosed within the outer perimeter of such object. For a spherical object, the area is thus computed based on the average diameter as 3.14×(diameter/2)$^2$. For a cylindrical object, the area is thus computed based on the average diameter and average length as diameter×length. For an irregularly shaped three-dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

Test 11: Density of the Sheet Article

Density of the flexible, porous, dissolvable solid sheet OCF article is determined by the equation: Calculated Density=Basis Weight of porous solid/(Porous Solid Thickness×1,000). The Basis Weight and Thickness of the dissolvable porous solid are determined in accordance with the methodologies described hereinabove.

Test 12: Specific Surface Area of the Sheet Article

The Specific Surface Area of the flexible, porous, dissolvable solid sheet OCF article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine Particle Technology", by Clyde Orr and Paul Webb.

Test 13: Moisture Vapor Transmission Rate (MVTR)

This test method is mostly performed according to ASTM F1249-13. The temperature of the test gas is set to 38° C. (±0.56° C.) and its relative humidity to 90% (±3%). The carrier gas is 100% $N_2$ (dry). The equipment used to run the test is a Permatran-W Water Vapor Permeability Instrument following the written procedure QMS 702-004. For materials outside of the Scope (§ 1.1) of ASTM F-1249-13, the water vapor transmission rate test method does not apply.

If the barrier properties of a specific substrate are too poor, especially if coatings on paper substrates were very thin and did not enable a good seal to the equipment, then it is not possible to measure the MVTR via ASTM F1249-13. In those cases, a different test method is used i.e. ASTM E96 Cup Test Method. However, results from the two different test methods can still be compared. For ASTM E96, the temperature was 38° C. and the relative humidity is 90%.

For either test method, the water vapor transmission rate is reported in g/m²/day. If normalized by the barrier thickness, the water vapor transmission rate is reported in g·μm/m²/day.

All MVTR tests were performed at Mocon Labs in Minneapolis.

Test 14: Oxygen Transmission Rate (OTR)

This test method is mostly performed according to ASTM F1927 under the following test conditions: The temperature of the test gas is 23° C. (±0.56° C.) and its relative humidity is 80% (±3%) and the test gas concentration is 100% O2. The carrier gas is 98% N2 and 2% H2 and the carrier gas humidity is 0%. Test gas pressure is 760 mmHg. The equipment used to carry out this test is the Oxtran 2/21 Oxygen Permeability Instrument following the test procedure QMS 702-002.

If the barrier properties of a specific substrate were too poor, especially if coatings on paper substrates were very thin and did not enable a good seal to the equipment, then it was not possible to measure the MVTR via ASTM F1927. In those cases, a different test method was used i.e. F3136. However, the results from the two different test methods can still be roughly compared.

For F3136, the temperature of the test gas is 23° C. (±0.56° C.) and its relative humidity is 39% and the test gas concentration is 20.9% O2 (room air). The equipment used to carry out this test is the Mocon OpTech-02 Model P Instrument following the test procedure QMS 702-002.

For either test method, the oxygen transmission rate is reported in cc/m2/day. If normalized by the barrier thickness, the water vapor transmission rate is reported in cc·μm/m2/day.

All OTR tests were performed at Mocon Labs in Minneapolis, USA.

Test 15: Grease Resistance Test (Kit Test)

Grease test resistance was measured using the TAPPI T 559 cm-12 Grease Resistance test for paper and paperboard. The grease tests were carried out at SGS Integrated Paper Services in Appleton, Wis., USA.

Samples were tested and conditioned in TAPPI standard conditions. Samples were not preconditioned.

| Room Conditions | | |
| --- | --- | --- |
| | Relative Humidity (%) | Temperature (° F.) |
| Condition Environment | 51.2 | 74.1 |
| Maximum during testing | 51.6 | 74.1 |
| | 51.2 | 73.9 |

TAPPI T 559 cm-12 Grease resistance test for paper and paperboard samples and specimens that passed Kit 12, are reported as greater than or equal to 12.

Unless specified differently, the KIT value reported is measured on the side facing the product (internal side).

Test 16: Overall Substrate/Individual Layers Thickness for the Overall Film/Individual Layers The thickness of the overall film/individual layers is measured by cutting a 20 μm thick cross-section of a film sample via sliding microtome (e.g. Leica SM2010 R), placing it under an optical microscope in light transmission mode (e.g. Leica Diaplan), and applying an imaging analysis software. Water-dispersible nanoplatelets layers contrast strongly with water-soluble polymeric layers. In case of adjacent water-soluble polymeric layers, the contrast can be achieved by adding different tracers such as 0.5% rhodamine B or 0.5% titan dioxide nanoparticles by weight.

Test 17: Film Tear Resistance.

This test method is performed according to ASTM D1922-15 (Elmendorf Method) using the equipment type and following the specimen preparation specified in the test method. The specimen has a substantially rectangular bottom portion and a semi-circular top portion. The bottom portion comprises a slit, which is pre-cut or applied in the instrument, extending towards the top portion 91 and has a length 20 mm in a direction perpendicular to the extension of a bottom edge and generally aligned to the film machine direction. The sample is attached between the two clamps. Then starts the pendulum and let it swing freely at least once. Stop the pendulum manually when there has been a break of the sample. The tear resistance shall be reported in mN.

Test 18: Caliper

The caliper, or thickness, of a single-layer test sample is measured under a static load by a micrometer, in accordance with compendial method ISO 534, with modifications noted herein. All measurements are performed in a laboratory maintained at 23° C.±2 C.° and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, Del., or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 mm$^2$ and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

Test 19: Basis Weight

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23° C.±2 C.° and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

Examples

Table 18 to Table 22 include examples of sachets that could be used for consumer products. The sachets are four-seal sachets. In these examples, the seal temperature can be 110-170° C., the seal time 0.5 seconds, and the seal pressure 3 bar. Whether or not a sachet was biodegradable, home compostable, and/or recyclable could be determined by testing the separate layers of the sachet materials and determining whether they meet the criteria as described herein. Acceptable package integrity, dry article integrity, and article performance were determined according to the Accelerated Stability Test.

TABLE 18

| | | Ex. 1 | Ex. 2 | Ex. 3 | Ex. 4 | Ex. 5 | Ex. 6 |
|---|---|---|---|---|---|---|---|
| Film | Outer Layer | 8 μm PET (polyethylene terephthalate) | — | 13-17 gsm beeswax from Sigma Aldrich ® | 19-45 μm cellulose NatureFlex ™ NKA from Futamura ® | 1945 μm NatureFlex ™ NKA cellulose from Futamura ® | 1945 μm NatureFlex ™ NMB cellulose form Futamura ® |
| | Middle Layer | 18 μm biaxially-oriented polypropylene | — | 80 gsm bleached kraft paper from B&B | — | 22 μm NatureFlex ™ NMB Cellulose from Futamura ® | — |
| | Inner Layer | 25 μm linear low-density polyethylene | 120 gsm PHA from Danimer ® | 80 μm PVOH (made from Selvol ™ 205 PVOH powder + 10% Glycerin + 10% Sorbitol) | — | 35 μm BioPBS ™ FD92M from Mitsubishi Chemical Corporation ™ | 80 μm PVOH (made from Selvol ™ 205 PVOH powder + 10% Glycerin + 10% Sorbitol) |
| Article Form | | Liquid Shampoo (Pantene ®, available in India 2019) | Liquid Shampoo (Pantene ®, available in India 2019) | Spun Fiber Shampoo (Table 2) | Spun Fiber Shampoo (Table 2) | Spun Fiber Shampoo (Table 2) | Spun Fiber Shampoo (Table 2) |
| Biodegradable | | No | Yes | Yes | Yes | No | Yes |
| Home compostable | | No | Yes | No data | Yes | Yes | Yes |
| Recyclable | | No | No | Yes | No | No | No |
| MVTR (g/sqm/day, at 38° C. and 90% RH) | | 0.17 ± 0.01 (ASTM F1249) | 37 ± 2 (ASTM F1249) | 12 ± 1 (ASTM E96-16) | 24 ± 5 (ASTM F1249) | 3.5 ± 1.5 (ASTM F1249) | 178 ± 5 (ASTM F1249) |
| OTR (cc/sqm/day at 23 C. and 80% RH) | | No data | No data | 169.5 ± 4.9 | 5.0 ± 0.5 (23 C., 50% RH) | <1 (23° C. 50% RH) | <1 (23° C. 50% RH) |
| KIT | | No data | No data | >12 | No data | >12 | >12 |
| Seal Strength | | Lock Seal >500 N/m | Hard Peel 250-500 N/m | Lock Seal >500 N/m | Easy Peel 75-200 N/m | Lock Seal >500 N/m | Lock Seal >500 N/m |

TABLE 18-continued

|  | Ex. 1 | Ex. 2 | Ex. 3 | Ex. 4 | Ex. 5 | Ex. 6 |
|---|---|---|---|---|---|---|
| Tear Resistance (mN) | 450~550 (benchmark) | Higher than benchmark | Lower than benchmark | Significantly lower than benchmark | Lower than benchmark | Lower than benchmark |
| Acceptable package integrity, dry article integrity, and article performance | Yes | No | No | No | No | No |

TABLE 19

|  |  | Ex. 7 | Ex. 8 | Ex. 9 | Ex. 10 | Ex. 11 | Ex. 12 |
|---|---|---|---|---|---|---|---|
| Film | Outer Layer | 19-45 μm NatureFlex ™ NKA cellulose form Futamura ® | 19-45 μm NatureFlex ™ NE cellulose form Futamura ® | 20 μm Cellulose | 19-45 μm cellulose NatureFlex ™ NKA from Futamura ® | 19-45 μm NatureFlex ™ NMB cellulose form Futamura ® | 19-45 μm NatureFlex ™ NKA cellulose form Futamura ® |
|  | Middle Layer | — | — | — | 22 μm NatureFlex ™ NMB cellulose form Futamura ® | — | — |
|  | Inner Layer | — | — | 15 μm BioPBS ™ FD92M from Mitsubishi Chemical Corporation ™ | 35 μm BioPBS ™ FD92M from Mitsubishi Chemical Corporation ™ | 80 μm PVOH (made from Selvol ™205 PVOH powder + 10% Glycerin + 10% Sorbitol) | 50 gsm PHA (solution coated or extrusion coated) from Danimer ® |
| Article Form |  | OCF Shampoo (Table 3) | OCF Shampoo (Table 3) | OCF Shampoo (Table 3) | OCF Shampoo (Table 3) | OCF Shampoo (Table 3) | OCF Shampoo (Table 3) |
| Biodegradable |  | Yes | Yes | Yes | Yes | Yes | Yes |
| Home compostable |  | Yes | Yes | Yes | Yes | Yes | Yes |
| Recyclable |  | No | No | No | No | No | No |
| MVTR (g/sqm/day, at 38° C. and 90% RH) |  | 24.0 ± 5 (ASTM F1249) | 732 ± 56 (ASTM F1249) | 691 ± 32 (ASTM F1249) | 3.5 ± 1.5 (ASTM F1249) | 178 ± 5 (ASTM F1249) | 23 ± 5 (ASTM F1249) |
| OTR (cc/sqm/day at 23° C. and 80% RH) |  | 5.0 ± 0.5 (23 C., 50% RH) | 13.9 ± 1.6 | 7.2 ± 0.5 | <1 (23° C. 50% RH) | <1 (23° C. 50% RH) | <5 (23 C., 50% RH) |
| KIT |  | No data | 6 | >12 | >12 | >12 | No data |
| Seal Strength |  | Easy Peel 75-200 N/m | Easy Peel 75-200 N/m | Lock Seal >500 N/m | Lock Seal >500 N/m | Lock Seal >500 N/m | Hard Peel 250-500 N/m |
| Tear Resistance (mN) |  | Significantly lower than benchmark | Significantly lower than benchmark | Lower than benchmark | Lower than benchmark | Lower than benchmark | Lower than benchmark |
| Acceptable package integrity, dry article integrity, and article performance |  | Yes | Yes | Yes | Yes | Yes | Yes |

Example 1 discloses a commercially available sachet used for liquid shampoo which is neither biodegradable, home compostable nor recyclable.

Most biodegradable or home compostable films are not compatible with liquid products. In Example 2, the sachet comprises 120 gsm PHA, which is biodegradable and home compostable. However, it was found that PHA films experience too high water loss over the shelf life (e.g. 6 months to 3 years) to be considered commercially viable for liquid products.

Examples 3, 4, 5, and 6 disclose various biodegradable and home compostable films used in combination with spun fiber articles. In these examples, the moisture barrier properties of the film were found insufficient to protect the spun fiber article, thus leading to poor dissolution and unacceptable article appearance and integrity over time.

Examples 7, 8, 9, 10, 11 and 12 disclose various sachet structures including cellulose films in combination with OCF articles. All of these films are both home compostable and biodegradable. In these examples, the sachets were found to have a relatively low tear resistance compared to the current laminate foil sachet enabling consumers to tear the sachet open only using their hands (i.e. without the use of teeth or scissors). Both Natureflex® NKA (example 7) and the Natureflex® NE cellulose (example 8) were found to be the easiest to open. However, these sachets have a weak peel force and can break open during distribution, especially if the sachet is pinched or compressed. Therefore, it can be desirable to include a PBSA or PHA or PVOH inner layer (examples 9, 10, 11 and 12). Even though the tearing force is a bit greater, it is still low enough to be consumer acceptable and is lower than the current multi-layer laminate sachet.

TABLE 20

| | | Ex. 19 | Ex. 20 | Ex. 21 | Ex. 22 | Ex. 23 | Ex. 24 |
|---|---|---|---|---|---|---|---|
| Film | Outer Layer | FybroZeal ® 63 gsm glassine From SCG Prepack ® (starch and water-based coating ≤10%) | 13-17 gsm beeswax from Sigma Aldrich ® | — | 25 gsm Paper supplied by Parkside ® | 7 gsm varnish supplied by Nippon Paper ® | — |
| | Middle Layer | — | PackPro 7.0 80 gsm Birgl & Bergmeister ® | PackPro 7.0 80 gsm Birgl & Bergmeister ® | 22 μm NatureFlex ™ NMB cellulose form Futamura ® | 62 gsm Shieldplus ™ Paper from Nippon Paper ® | PackPro 7.0 80 gsm Birgl & Bergmeister ® |
| | Inner Layer | — | PVOH 5 μm (made from Selvol ™ 205 PVOH powder + 10% Glycerin + 10% Sorbitol) | 30 μm BioPBSA ™ FD92M from Mitsubishi Chemical Corporation ™ | 30 μm BioPBS ™ FD92M from Mitsubishi Chemical Corporation ™ | 30 μm BioPBS ™ FD92M from Mitsubishi Chemical Corporation ™ | PVOH 80 μm (made from Selvol ™ 205 PVOH powder + 10% Glycerin + 10% Sorbitol) |
| Article Form | | OCF Shampoo (Table 3) | OCF Shampoo (Table 3) | OCF Shampoo (Table 3) | OCF Shampoo (Table 3) | OCF Shampoo (Table 3) | OCF Shampoo (Table 3) |
| Biodegradable | | Yes | Yes | Yes | Yes | Yes | Yes |
| Home compostable | | No data | No data | No data | Yes | No data | No data |
| Recyclable | | Yes (internal SCG protocol) | No data | No | No data | No data | Yes |
| MVTR (g/sqm/day, at 38° C. and 90% RH) | | 1623 ± 110 (ASTM E96-16) | 138 ± 24 (ASTM E96-16) | 738 ± 20 (ASTM E96-16) | 38 ± 12 (ASTM E96-16) | 62 ± 3 (ASTM E96-16) | 650 +/− 150 (ASTM E96-16) |
| OTR (cc/sqm/day at 23 C. and 80% RH) | | No data | No data | No data | <1 (23° C. 50% RH) | 1100 ± 100 | No data |
| KIT | | <6 | No data | >12 | >12 | >12 | >12 |
| Seal Strength | | Hard Peel 250-500 N/m | Easy Peel 75-200 N/m | Lock Seal >500 N/m | Lock Seal >500 N/m | Lock Seal >500 N/m | Lock Seal >500 N/m |
| Tear Resistance (mN) | | Significantly lower than benchmark | Significantly lower than benchmark | Significantly lower than benchmark | Significantly lower than benchmark | Significantly lower than benchmark | Lower than benchmark |
| Acceptable package integrity, dry article integrity, and article performance | | No (Surfactant Leaching) | No (Surfactant Leaching) | Yes | Yes | Yes | Yes |

TABLE 21

| | | Ex. 25 | Ex. 26 | Ex. 27 | Ex. 28 |
|---|---|---|---|---|---|
| Film | Outer Layer | Propack 7.0 80 gsm bleached kraft paper from B&B ® | Propack 7.0 80 gsm bleached kraft paper from B&B ® | Prepack 7.0 80 gsm bleached kraft paper from B&B ® | Propack 7.0 80 gsm bleached kraft paper from B&B ® |
| | 1st Middle Layer | PVOH 9 μm (made from Selvol ™ 205 PVOH powder + 10% Glycerin + 10% Sorbitol) | PVOH 9 μm (made from Selvol ™ 205 PVOH powder + 10% Glycerin + 10% Sorbitol) | PVOH 9 μm (made from Selvol ™ 205 PVOH powder + 10% Glycerin + 10% Sorbitol) | PVOH 9 μm (made from Selvol ™ 205 PVOH powder + 10% Glycerin + 10% Sorbitol) |
| | 2nd Middle Layer | Aluminum 100 μm from Fraunhofer ® (vapor deposition) | Bio-Ormocer 6 μm from Fraunhofer ® (solution coating) | Bio-Ormocer 6 μm from Fraunhofer ® (solution coating) | Bio-Ormocer 6 μm from Fraunhofer ® (solution coating) |
| | 3rd Middle Layer | — | Aluminum 100 μm from Fraunhofer ® (vapor deposition) | Aluminum 100 μm from Fraunhofer ® (vapor deposition) | Aluminum 100 μm from Fraunhofer ® (vapor deposition) |
| | 4th Middle Layer | — | Bio-Ormocer 3.5 μm from Fraunhofer ® (solution coating) | Bio-Ormocer 3.5 μm from Fraunhofer ® (solution coating) | Bio-Ormocer 3.5 μm from Fraunhofer ® (solution coating) |
| | Inner Layer | PVOH 18 μm (made from Selvol ™ 205 PVOH powder + 10% Glycerin + 10% Sorbitol) | PVOH 18 μm (made from Selvol ™ 205 PVOH powder + 10% Glycerin + 10% Sorbitol) | 15 μm BioPBS ™ FD92M from Mitsubishi Chemical Corporation ™ | 11 μm BioPBS ™ FD92M from Mitsubishi Chemical Corporation ™ |
| Article Form | | OCF Shampoo (Table 3) | OCF Shampoo (Table 3) | OCF Shampoo (Table 3) | OCF Shampoo (Table 3) |
| Biodegradable | | Yes | Yes | Yes | Yes |
| Home compostable | | No data | No data | No data | No data |
| Recyclable | | Yes | Yes | Yes | Yes |
| MVTR (g/sqm/day, at 38° C. and 90% RH) | | 264 ± 20 (ASTM E96-16) | 1.22 ± 0.1 (ASTME96-16) | 4.0 ± 0.5 (ASTM E96-16) | 4.0 ± 0.5 (ASTM E96-16) |

TABLE 21-continued

|  | Ex. 25 | Ex. 26 | Ex. 27 | Ex. 28 |
|---|---|---|---|---|
| OTR (cc/sqm/day at 23 C. and 80% RH) | 13.8 ± 0.1 | <0.005 | 7.14 ± 0.7 | No data |
| KIT | >12 | >12 | >12 | >12 |
| Seal Strength | Lock Seal | Lock Seal | Lock Seal | Easy Peel 75-200 N/m |
| Tear Resistance (mN) | Lower than benchmark | Lower than benchmark | Lower than benchmark | Lower than benchmark |
| Acceptable package integrity, dry article integrity, and article performance | Yes | Yes | Yes | Yes |

TABLE 22

|  |  | Ex. 29 | Ex. 30 | Ex. 31 | Ex. 32 | Ex. 33 | Ex. 34 |
|---|---|---|---|---|---|---|---|
| Film | Outer Layer | 17 gsm beeswax from Sigma Aldrich ® | 17 gsm beeswax from Sigma Aldrich ® | 17 gsm beeswax from Sigma Aldrich ® | 5 gsm beeswax from Sigma Aldrich ® | 10 gsm beeswax from Sigma Aldrich ® | 4 gsm Caranauba wax from Alfa Aesar ® |
|  | Middle Layer | PackPro 7.0 80 gsm Birgl & Bergmeister ® | PackPro 7.0 80 gsm Birgl & Bergmeister ® | 80 gsm Leine Nature ® paper from Sappi ® | PackPro 7.0 80 gsm Birgl & Bergmeister ® | PackPro 7.0 80 gsm Birgl & Bergmeister ® | PackPro 7.0 80 gsm Birgl & Bergmeister ® |
|  | Inner Layer | PVOH 80 μm (made from Selvol ™ 205 PVOH powder + 10% Glycerin + 10% Sorbitol) | PHA 50 gsm (solution coated or extrusion coated) from Danimer ® | PVOH 80 μm (made from Selvol ™ 205 PVOH powder + 10% Glycerin + 10% Sorbitol) | PVOH 80 μm (made from Selvol ™ 205 PVOH powder + 10% Glycerin + 10% Sorbitol) | PVOH 80 μm (made from Selvol ™ 205 PVOH powder + 10% Glycerin + 10% Sorbitol) | PVOH 44 gsm (made from Selvol ™ 205 PVOH powder + 10% Glycerin + 10% Sorbitol) |
| Article Form |  | OCF Shampoo (Table 3) | OCF Shampoo (Table 3) | OCF Shampoo (Table 3) | OCF Shampoo (Table 3) | OCF Shampoo (Table 3) | OCF Shampoo (Table 3) |
| Biodegradable |  | Yes | Yes | Yes | Yes | Yes | Yes |
| Home compostable |  | No data | No data | No data | No data | No data | No data |
| Recyclable |  | No data | No data | No data | No data | No data | Yes |
| MVTR (g/sqm/day, at 38° C. and 90% RH) |  | 12 ± 1 (ASTM E96-16) | 11.5 ± 1.5 (ASTM E96-16) | 12 ± 1 (ASTM E96-16) | 176 ± 39 (ASTM E96-16) | 48 ± 17 (ASTM E96-16) | 33 ± 2 (ASTM E96-16) |
| OTR (cc/sqm/day at 23° C. and 80% RH |  | 169.5 ± 4.9 | No data | No data | No data | No data | 9.5 ± 1.0 |
| KIT |  | >12 | No data | >12 | >12 | >12 | >12 |
| Seal Strength |  | Lock Seal >500 N/m | Hard Peel 250-500 N/m | Lock Seal >500 N/m | Lock Seal >500 N/m | Lock Seal >500 N/m | Lock Seal >500 N/m |
| Tear Resistance (mN) |  | Lower than benchmark | Lower than benchmark | Lower than benchmark | Lower than benchmark | Lower than benchmark | Lower than benchmark |
| Acceptable package integrity, dry article integrity, and article performance |  | Yes | Yes | Yes | Yes | Yes | Yes |

Examples 19-34 in Table 20 to Table 22 disclose various sachet structures including paper films in combination with OCF articles. These sachets structures are both biodegradable and/or home compostable, and/or recyclable. Examples 19 and 20 disclose paper sachets structures that are biodegrable but vulnerable to surfactant leaching when exposed to high storage temperature and high relative humidity. It was found that the presence of a moisture barrier layer and/or a grease barrier layer between the product can be added to stop or significantly slow down surfactant leaching to an acceptable level.

Examples 21-34 disclose various biodegradable sachet structures including paper films in combination with OCF articles which delivered a satisfactory stability performance. All of these structures include either a PBSA or PHA or PVOH inner layer. Examples 24, 25, 26, 28 and 34 disclose biodegradable sachet paper structures which were also found to be recyclable. Example 22 discloses a biodegradable sachet paper structure which was proven to be home compostable. It was found that the addition of a biodegradable wax such as beeswax (examples 29, 30, 31, 32, 33) or carnauba wax 34 can be beneficial to provide some water splash resistance, which is desirable to provide a additional barrier, since these sachets can be displayed in high frequency stored in an open environment. In Example 31, Leine Nature® paper is thought to have a particularly fast biodegradation rate.

Combinations:
  A. A sachet product comprising a biodegradable and/or home compostable sachet comprising a front film and a back film comprising:
    a. a front middle layer and a back middle layer comprising a paper with greater than 85% cellulose;
    b. a front inner layer joined to the front middle layer and a back inner layer joined to the back middle layer wherein the front inner layer and back inner layer comprises an inner layer material selected from the group consisting of polyvinyl alcohol, polybutylene succinate, polybutylene succinate adipate, polyhydroxylalkonate, polyvinylidene chloride, carnauba wax, biodegradable thermo-plastic starch, and combinations thereof;
    wherein front inner layer and back inner layer being permanently joined around a perimeter to form a seal, the seal forming a compartment adapted for storing a solid article comprising an open cell foam comprising:
- from about 10% to about 40%, preferably from about 15% to about 30%, more preferably from about 20% to about 25%, by total weight of the article, of a water-soluble polymer;
- from about 5% to about 80%, alternatively from about 10% to about 70%, alternatively from about 30% to about 65%, by total weight of the article, surfactant selected from the group consisting of anionic surfactants, cationic surfactants, nonionic surfactants, amphoteric surfactants, zwitterionic surfactants, and combinations thereof;
- a Percent Open Cell Content of from about 80% to 100%, preferably from about 85% to 100%, and more preferably from about 90% to 100% as measured according to Test 3;
- an Overall Average Pore Size of from about 100 μm to about 2000 μm, alternatively from about 150 μm to about 1000 μm, alternatively from about 200 μm to about 600 μm, as measured by the Micro-CT method described in Test 2.

B. The sachet product of paragraph A, wherein the front film and the back film further comprise front outer layer joined to front middle layer and back outer layer joined to back middle layer wherein front film and back film comprise a biodegradable wax.

C. The sachet product of paragraph B, wherein the biodegradable wax is selected from the group consisting of beeswax, jojoba wax, carnauba wax, and combinations thereof.

D. The sachet product of paragraphs A to C, wherein the paper further comprises a vegetable oil binder.

E. The sachet product of paragraphs A to D, wherein the inner layer material comprises polyvinyl alcohol.

F. The sachet product of paragraphs A to E, wherein the front middle layer and back middle layer comprise a grammage of from about 30 to about 120 gsm, preferably from about 40 to about 110 gsm, more preferably from about 50 to about 100 gsm, and even more preferably from about 60 to about 90 gsm.

G. A sachet product comprising a biodegradable and/or home compostable sachet comprising a front film and a back film comprising:
  a. a front outer layer and a back outer layer comprising cellulose;
  b. a front inner layer joined to the front outer layer and a back outer layer joined to the back outer layer wherein the front inner layer and the back outer layer comprise a material selected from the group consisting of polyvinyl alcohol, polybutylene succinate, polybutylene succinate adipate, polyhydroxylalkonate, carnauba wax, a biodegradable thermo-plastic starch, polyvinylidene chloride, and combinations thereof;
  wherein front inner layer and back inner layer being permanently joined around a perimeter to form a seal, the seal forming a compartment adapted for storing a solid article comprising an open cell foam comprising:
    from about 10% to about 40%, preferably from about 15% to about 30%, more preferably from about 20% to about 25%, by total weight of the article, of a water-soluble polymer;
    from about 5% to about 80%, alternatively from about 10% to about 70%, alternatively from about 30% to about 65%, by total weight of the article, surfactant selected from the group consisting of anionic surfactants, cationic surfactants, nonionic surfactants, amphoteric surfactants, zwitterionic surfactants, and combinations thereof;
    a Percent Open Cell Content of from about 80% to 100%, preferably from about 85% to 100%, and more preferably from about 90% to 100% as measured according to Test 3;
    an Overall Average Pore Size of from about 100 μm to about 2000 μm, alternatively from about 150 μm to about 1000 μm, alternatively from about 200 μm to about 600 μm, as measured by the Micro-CT method described in Test 2.

H. The sachet product of paragraphs A to G, wherein front outer layer and back outer layer comprise a thickness from about 5 μm to about 50 μm, preferably from about 10 μm to about 40 μm, and more preferably from about 15 μm to about 30 μm.

I. The sachet product of paragraphs A to H, wherein the front inner layer and the back inner layer comprise a thickness from about 1 μm to about 150 μm, preferably from about 2 μm to about 100 μm, more preferably from about 3 μm to about 40 μm, and even more preferably from about 10 μm to about 30 μm.

J. The sachet product of paragraphs A to I, wherein the sachet is biodegradable and compostable.

K. The sachet product of paragraphs A to J, wherein the sachet is recyclable.

L. The sachet product of paragraphs A to K, wherein the sachet is a four-seal sachet.

M. The sachet product of paragraphs A to L, wherein the sachet product comprises an MVTR of from about 0.01 to about 50 g/sqm/day, preferably of from about 0.05 to about 40 g/sqm/day, of from about 0.1 to about 30 g/sqm/day, and even more preferably of from about 0.2 to about 15 g/sqm/day as measured according to ASTM E96-16.

N. The sachet product of paragraphs A to M, wherein the sachet comprises a tear resistance of less than 550 nM according to D1922-15, Elmendorf Method, MD tear direction.

O. The sachet product of paragraphs A to N, wherein the seal comprises a seal strength of from about 250 to about 700 N/m, alternatively from about 300 to about 600 N/m, alternatively from about 300 to about 500 N/m according to ASTM F88-15 at 300 mm/min and 2.95 bar (295 kPa).

P. The sachet product of paragraphs A to O, wherein the sachet product satisfies the Seal Test.

Q. The sachet product of paragraphs A to P, where after 2 weeks of storage at 40° C., 75% RH the article can have a Hand Dissolution value of less than 15 strokes, preferably less than 12 strokes, and most preferably less than 10 strokes according to the Hand Dissolution Test Method.

R. The sachet product of paragraphs A to Q, wherein after storage for a period of 2 weeks, preferably 4 weeks, more preferably 8 weeks, more preferably 12 weeks, and most preferably 6 months, the sachet product can satisfy the Accelerated Stability Test.

S. The sachet product of paragraphs A to R, wherein after storage for a period of 2 weeks, preferably 4 weeks, more preferably 8 weeks, more preferably 12 weeks, and most preferably 6 months, the sachet product can satisfy the Stability Test.

T. The sachet product of paragraphs A to S, wherein the sachet product is a consumer product selected from the group consisting of laundry detergent products, fabric softening products, hand cleansing products, hair shampoo products, hair conditioning products, hair styling products, body cleansing products, shaving preparation products, dish cleaning products, skin care products, moisturizing products, sunscreen products, beauty products, deodorizing products, oral care products, feminine cleansing products, baby care products, fragrance-containing products, and combinations thereof.

U. The sachet product of paragraphs A to T, wherein the article comprises an Average Cell Wall Thickness of from about 5 μm to about 200 μm, preferably from about 10 μm to about 100 μm, more preferably from about 10 μm to about 80 μm, as measured by Test 2.

V. The sachet product of paragraphs A to U, wherein the article comprises a final moisture content of from about 0.5% to about 25%, preferably from about 1% to about 20%, more preferably from about 3% to about 10%, by weight of said solid sheet OCF article, as measured by Test 4 hereinafter.

W. The sachet product of paragraphs A to V, wherein the article comprises a density ranging from about 0.05 g/cm³ to about 0.5 g/cm³, preferably from about 0.06 g/cm³ to about 0.4 g/cm³, more preferably from about 0.07 grams/cm³ to about 0.2 grams/cm³, most alternatively from about 0.08 grams/cm³ to about 0.15 grams/cm³, as measured by Test 7 hereinafter.

X. The sachet product of paragraphs A to W, wherein the article comprises a Specific Surface Area of from about 0.03 m²/g to about 0.25 m²/g, preferably from about 0.04 m²/g to about 0.22 m²/g, more preferably from 0.05 m²/g to 0.2 m²/g, most preferably from 0.1 m²/g to 0.18 m²/g, as measured by Test 8 described hereinafter.

Y. The sachet product of paragraphs A to X, wherein the water-soluble polymer comprises a weight average molecular weights from about 50,000 to about 400,000 Daltons, preferably from about 60,000 to about 300,000 Daltons, more preferably from about 70,000 to about 200,000 Daltons, and most preferably from about 80,000 to about 150,000 Daltons.

Z. The sachet product of paragraphs A to Y, wherein the water-soluble polymer is selected from the group consisting of polyvinyl alcohols, polyvinylpyrrolidones, polyalkylene oxides, starch and starch derivatives, pullulan, gelatin, hydroxypropylmethylcelluloses, methylcelluloses, and carboxymethylcelluloses. In another example, water-soluble polymers may include polyvinyl alcohols, hydroxypropylmethylcelluloses, and combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sachet product comprising a solid article comprising an open cell foam and an ultimate biodegradable sachet comprising a front film and a back film comprising:
   a. a front middle layer and a back middle layer comprise a material selected from the group consisting of cellulose, cellulose acetate, metalized cellulose, metalized cellulose acetate, and combinations thereof;
   b. a front inner layer joined to the front middle layer and a back inner layer joined to the back middle layer wherein the front inner layer and the back inner layer comprise a material selected from the group consisting of polyvinyl alcohol, polybutylene succinate, polybutylene succinate adipate, polyhydroxylalkonate, carnauba wax, a biodegradable thermo-plastic starch, polyvinylidene chloride, and combinations thereof;
   wherein the sachet comprises a MVTR of from about 12 to about 800 g/sqm/day at 38° C. and 90% RH;
   wherein the front inner layer and the back inner layer being permanently joined around a perimeter to form a seal, the seal forming a compartment adapted for storing the solid article wherein the open cell foam comprises:
   a water-soluble polymer;
   a surfactant selected from the group consisting of anionic surfactants, cationic surfactants, nonionic surfactants, amphoteric surfactants, zwitterionic surfactants, and combinations thereof;
   a Percent Open Cell Content of from about 80% to 100%;
   an Overall Average Pore Size of from about 100 μm to about 2000 μm.

2. The sachet product of claim 1, wherein the sachet is home compostable.

3. The sachet product of claim 1, wherein after storage for a period of 2 weeks the sachet product can satisfy the Accelerated Stability Test.

4. The sachet product of claim 1, wherein the sachet further comprises a front outer layer joined to the front middle layer and a back outer layer joined to the back middle layer; wherein the front outer layer and the back outer layer comprise paper having greater than 85% cellulose content.

5. The sachet product of claim 1, wherein the front inner layer and/or the back inner layer comprises polybutylene succinate adipate and wherein the polybutylene succinate adipate is metalized.

6. The sachet product of claim 1, further comprising a front biodegradable adhesive layer between the front middle layer and the front inner layer and a back biodegradable adhesive layer between the back middle layer and the back inner layer.

7. The sachet product of claim 1, wherein the front film and the back film further comprise a front outer layer joined to the front middle layer and a back outer layer joined to the back middle layer wherein front outer layer and back outer layer comprise a biodegradable wax.

8. The sachet product of claim 7, wherein the biodegradable wax is selected from the group consisting of beeswax, jojoba wax, carnauba wax, rapeseed wax, castor wax, candelilla wax, soy wax, palm oil wax, and combinations thereof.

9. The sachet product of claim 1, wherein the inner layer material comprises polyvinyl alcohol and/or polyhydroxylalkonate.

10. The sachet product of claim 1, wherein the sachet is recyclable.

11. The sachet product of claim 1, wherein the sachet is a four-seal sachet.

12. The sachet product of claim 1, wherein the sachet comprises a tear resistance of less than 550 nM.

13. The sachet product of claim 1, wherein the seal comprises a seal strength of greater than 500 N/m.

14. The sachet product of claim 1, where after 2 weeks of storage at 40° C., 75% RH the article comprises a Hand Dissolution value of less than 15 strokes and a final moisture content of from about 0.5% to about 25%.

15. The sachet product of claim 1, wherein the front middle layer and back middle layer comprise a grammage of from about 30 to about 120 gsm.

16. The sachet product of claim 1, wherein the front inner layer and the back inner layer comprise a thickness from about 3 μm to about 40 μm.

17. The sachet product of claim 1, wherein the water-soluble polymer is selected from the group consisting of polyvinyl alcohols, polyvinylpyrrolidones, polyalkylene oxides, starch and starch derivatives, pullulan, gelatin, hydroxypropylmethylcelluloses, methylcelluloses, carboxymethycelluloses, and combinations thereof.

18. The sachet product of claim 1, wherein the front inner layer and the back inner layer comprise a grease resistance greater than 6.

19. The sachet product of claim 1, further comprising an additional layer joined between the front middle layer and the front inner layer and an additional layer joined between the back middle layer and the back inner layer wherein the additional layers comprise an MVTR less than 300 g/m$^2$/day at 38° C. and 98% RH.

20. The sachet product of claim 1, comprising from about 10% to about 40%, by weight of the article, of the water-soluble polymer and from about 5% to about 80%, by total weight of the article, of the surfactant.

\* \* \* \* \*